US005843063A

United States Patent [19]

Anderson et al.

[11] Patent Number: 5,843,063
[45] Date of Patent: Dec. 1, 1998

[54] MULTIFUNCTIONAL ABSORBENT MATERIAL AND PRODUCTS MADE THEREFROM

[75] Inventors: Richard Allen Anderson, Roswell; Andrew Scott Burnes, Lawrenceville; Kuo-Shu Edward Chang, Roswell; Stanley Michael Gryskiewicz, Woodstock; Connie Lynn Hetzler; Margaret Gwyn Latimer, both of Alpharetta, all of Ga.; Yong Li, Appleton, Wis.; Sylvia Bandy Little, Marietta, Ga.; Tamara Lee Mace, Doraville, Ga.; Billie Jean Matthews, Woodstock, Ga.; James Brian Riddle, Dandridge, Tenn.; Lawrence Howell Sawyer, Roswell, Ga.; Hoa La Wilhelm, Appleton, Wis.

[73] Assignee: Kimberly-Clark Worldwide, Inc., Neenah, Wis.

[21] Appl. No.: 754,414

[22] Filed: Nov. 22, 1996

[51] Int. Cl.$^6$ ...................................................... A61F 13/15
[52] U.S. Cl. ............................................ 604/378; 428/218
[58] Field of Search ............................ 428/218; 604/378, 604/385, 368, 360

[56] References Cited

U.S. PATENT DOCUMENTS

| | | | |
|---|---|---|---|
| H1377 | 11/1994 | Perry ..................................... | 604/385.1 |
| H1511 | 12/1995 | Chappell et al. ........................ | 604/383 |
| Re. 32,957 | 6/1989 | Elias ....................................... | 604/368 |
| 3,338,992 | 8/1967 | Kinney .................................... | 264/24 |
| 3,341,394 | 9/1967 | Kinney .................................... | 161/72 |
| 3,502,763 | 3/1970 | Hartmann ............................... | 264/210 |
| 3,542,615 | 11/1970 | Dobo et al. .............................. | 156/181 |
| 3,692,618 | 9/1972 | Dorschner et al. ..................... | 161/72 |
| 3,768,480 | 10/1973 | Mesek et al. ........................... | 128/287 |
| 3,802,817 | 4/1974 | Matsuki et al. ......................... | 425/66 |
| 3,849,241 | 11/1974 | Butin et al. ............................. | 161/169 |
| 4,050,462 | 9/1977 | Woon et al. ............................. | 128/287 |
| 4,213,459 | 7/1980 | Sigl et al. ............................... | 128/287 |
| 4,333,463 | 6/1982 | Holtman ................................. | 128/287 |
| 4,340,563 | 7/1982 | Appel et al. ............................ | 264/518 |
| 4,381,783 | 5/1983 | Elias ....................................... | 604/368 |
| 4,397,644 | 8/1983 | Matthews et al. ...................... | 604/378 |
| 4,413,032 | 11/1983 | Hartmann et al. ...................... | 428/288 |
| 4,413,996 | 11/1983 | Taylor .................................... | 604/382 |
| 4,480,000 | 10/1984 | Watanabe et al. ...................... | 428/284 |
| 4,500,315 | 2/1985 | Pieniak et al. .......................... | 604/379 |
| 4,531,945 | 7/1985 | Allison ................................... | 604/378 |
| 4,537,590 | 8/1985 | Pieniak et al. .......................... | 604/379 |
| 4,540,414 | 9/1985 | Wishman ................................ | 604/378 |
| 4,560,372 | 12/1985 | Pieniak ................................... | 604/369 |
| 4,568,341 | 2/1986 | Mitchell et al. ........................ | 604/368 |
| 4,573,988 | 3/1986 | Pieniak et al. .......................... | 604/379 |
| 4,578,070 | 3/1986 | Hoitman ................................. | 604/378 |
| 4,585,448 | 4/1986 | Enloe ..................................... | 604/378 |
| 4,605,402 | 8/1986 | Iskra ....................................... | 604/368 |
| 4,636,209 | 1/1987 | Lassen ................................... | 604/378 |
| 4,637,819 | 1/1987 | Quellette et al. ....................... | 604/369 |
| 4,650,479 | 3/1987 | Insley ..................................... | 604/358 |
| 4,655,757 | 4/1987 | McFarland et al. .................... | 604/366 |
| 4,670,011 | 6/1987 | Mesek .................................... | 604/378 |
| 4,673,402 | 6/1987 | Weisman et al. ....................... | 604/368 |
| 4,676,784 | 6/1987 | Erdman et al. ......................... | 604/368 |

(List continued on next page.)

FOREIGN PATENT DOCUMENTS

| | | | |
|---|---|---|---|
| 2147685 | 2/1996 | Canada ........................... | A61F 13/54 |
| 0 217 666 | 4/1987 | European Pat. Off. . | |
| 0 481 322 A1 | 4/1992 | European Pat. Off. . | |
| 0 518 291 A1 | 12/1992 | European Pat. Off. . | |
| 0 539 703 A1 | 5/1993 | European Pat. Off. . | |
| 0 606 208 B1 | 7/1994 | European Pat. Off. . | |
| 0 631 768 | 1/1995 | European Pat. Off. . | |
| 0 640 330 | 3/1995 | European Pat. Off. . | |
| 0 670 154 | 9/1995 | European Pat. Off. . | |
| 0 692 230 A1 | 1/1996 | European Pat. Off. . | |

(List continued on next page.)

OTHER PUBLICATIONS

*Polymer Blends and Composites,* John A. Manson and Leslie H. Sperling, copyright 1976, Plenum Press, ISBN–0–306–30831–2, pp. 273–277.

Article by R.W. Hoyland and R. Field in *Paper Technology and Industry,* Dec. 1976, pp. 291–299 and *Porous Media Fluid Transport and Pore Structure,* F.A.L. Dullien, 1979, Academic Press, Inc. ISBN 0–12–223650–5.

Article, "Fluid Distribution: Comparison of X–Ray Imaging Data," David F. Ring, Oscar Lijap and Jospeh Pascente in *Nonwovens World* magazine, Summer '95, pp. 65–70.

*Textile Science and Technology,* vol. 7, Pronoy K. Chatterjee, Elsevier Science Publishers B.V. 1985, ISBN 0–444–42377–X (vol. 7), Chapters 2, 4, 5.

Docket No.: 10,060.1, entitled "Absorbent Structure Comprising Superabsorbent, Staple Fiber, and Binder Fiber".

Research Disclosure 37421, "Thermally Bonded Absorbent Structures Having Discrete, Stepped Density Zones in the Z–Dimension," Jun. 1995, Inventor—Anonymous, Class/Subclass: 156/298.

*Primary Examiner*—Robert A. Clarke
*Attorney, Agent, or Firm*—James B. Robinson

[57] ABSTRACT

A multifunctional material is provided for use in personal care products. The multifunctional material has a permeability between 100 and 10000 Darcys and a capillary tension between about 2 and 15 cm. Structures containing this multifunctional material can have a runoff rate of less than 25 ml per 100 ml insult, over its life. The multifunctional material should have between about 30 and 75 weight percent of a slow rate superabsorbent, between 25 and 70 weight percent of pulp and from a positive amount up to about 10 percent of a binder component. The material preferably has a density between about 0.05 and 0.5 g/cc. The material has a liquid pass through function which desorbs a surge material across time frames consistent with user conditions and releases the liquid for distribution to remote storage locations. The material, when combined with the intake and distribution materials, defines a composite structure for use in personal care products.

20 Claims, 5 Drawing Sheets

U.S. PATENT DOCUMENTS

| | | | |
|---|---|---|---|
| 4,681,577 | 7/1987 | Stern et al. | 604/378 |
| 4,685,914 | 8/1987 | Holtman | 604/368 |
| 4,685,915 | 8/1987 | Hasse et al. | 604/378 |
| 4,699,619 | 10/1987 | Bernardin | 604/378 |
| 4,699,620 | 10/1987 | Bernardin | 604/385 A |
| 4,699,823 | 10/1987 | Kellenberger et al. | 428/219 |
| 4,723,953 | 2/1988 | Rosenbaum et al. | 604/369 |
| 4,755,178 | 7/1988 | Insley et al. | 604/367 |
| 4,778,459 | 10/1988 | Fuisz | 604/378 |
| 4,781,710 | 11/1988 | Megison et al. | 604/378 |
| 4,787,896 | 11/1988 | Houghton et al. | 604/385.1 |
| 4,798,603 | 1/1989 | Meyer et al. | 604/378 |
| 4,834,735 | 5/1989 | Alemany et al. | 604/368 |
| 4,842,594 | 6/1989 | Ness | 604/368 |
| 4,880,419 | 11/1989 | Ness | 604/368 |
| 4,885,201 | 12/1989 | Bither et al. | 428/284 |
| 4,888,231 | 12/1989 | Angstadt | 428/213 |
| 4,892,528 | 1/1990 | Suzuki et al. | 604/385.2 |
| 4,892,532 | 1/1990 | Boman | 604/366 |
| 4,892,534 | 1/1990 | Datta et al. | 604/370 |
| 4,892,535 | 1/1990 | Bjornberg et al. | 604/380 |
| 4,904,249 | 2/1990 | Miller et al. | 604/378 |
| 4,908,026 | 3/1990 | Sukiennik et al. | 604/378 |
| 4,923,454 | 5/1990 | Seymour et al. | 604/368 |
| 4,935,022 | 6/1990 | Lash et al. | 604/368 |
| 4,938,756 | 7/1990 | Salek | 604/368 |
| 4,950,264 | 8/1990 | Osborn, III | 604/385.1 |
| 4,961,982 | 10/1990 | Taylor | 428/41 |
| 4,988,344 | 1/1991 | Reising et al. | 604/368 |
| 4,988,345 | 1/1991 | Reising | 604/368 |
| 4,994,037 | 2/1991 | Bernardin | 604/368 |
| 5,009,650 | 4/1991 | Bernardin | 604/378 |
| 5,009,653 | 4/1991 | Osborn, III | 604/385.1 |
| 5,013,309 | 5/1991 | Baigas, Jr. et al. | 604/368 |
| 5,021,050 | 6/1991 | Iskra | 604/379 |
| 5,030,229 | 7/1991 | Yang | 604/385.1 |
| 5,037,409 | 8/1991 | Chen et al. | 604/358 |
| 5,043,206 | 8/1991 | Ternström | 428/218 |
| 5,047,023 | 9/1991 | Berg | 604/368 |
| 5,057,368 | 10/1991 | Largman et al. | 428/397 |
| 5,062,839 | 11/1991 | Anderson | 604/385.1 |
| 5,069,970 | 12/1991 | Largman et al. | 428/373 |
| 5,098,423 | 3/1992 | Pieniak et al. | 604/385.1 |
| 5,108,820 | 4/1992 | Kaneko et al. | 428/198 |
| 5,108,827 | 4/1992 | Gessner | 428/219 |
| 5,124,188 | 6/1992 | Roe et al. | 428/72 |
| 5,124,197 | 6/1992 | Bernardin et al. | 428/284 |
| 5,134,007 | 7/1992 | Reising et al. | 428/78 |
| 5,147,345 | 9/1992 | Young et al. | 604/378 |
| 5,149,334 | 9/1992 | Lahrman et al. | 604/367 |
| 5,149,335 | 9/1992 | Kellenberger et al. | 604/372 |
| 5,151,091 | 9/1992 | Glaug et al. | 604/385.1 |
| 5,171,391 | 12/1992 | Chmielewski et al. | 156/229 |
| 5,176,668 | 1/1993 | Bernardin | 604/368 |
| 5,176,672 | 1/1993 | Bruemmer et al. | 604/385.1 |
| 5,188,624 | 2/1993 | Young, Sr. et al. | 604/378 |
| 5,192,606 | 3/1993 | Proxmire et al. | 428/284 |
| 5,200,248 | 4/1993 | Thompson et al. | 428/131 |
| 5,217,445 | 6/1993 | Young et al. | 604/381 |
| 5,236,427 | 8/1993 | Hamajima et al. | 604/378 |
| 5,242,435 | 9/1993 | Murji et al. | 604/374 |
| 5,248,309 | 9/1993 | Serbiak et al. | 604/368 |
| 5,252,374 | 10/1993 | Larsonneur | 428/77 |
| 5,257,982 | 11/1993 | Cohen et al. | 604/378 |
| 5,277,976 | 1/1994 | Hogle et al. | 428/397 |
| 5,281,207 | 1/1994 | Chmielewski et al. | 604/378 |
| 5,281,208 | 1/1994 | Thompson et al. | 604/378 |
| 5,294,478 | 3/1994 | Wanek et al. | 428/218 |
| 5,300,054 | 4/1994 | Feist et al. | 607/378 |
| 5,304,161 | 4/1994 | Noel et al. | 604/378 |
| 5,318,553 | 6/1994 | Weeks et al. | 604/378 |
| 5,318,554 | 6/1994 | Young et al. | 604/378 |
| 5,330,457 | 7/1994 | Cohen | 604/378 |
| 5,334,176 | 8/1994 | Buenger et al. | 604/367 |
| 5,334,177 | 8/1994 | Cohen | 604/378 |
| 5,336,552 | 8/1994 | Strack et al. | 428/224 |
| 5,342,334 | 8/1994 | Thompson et al. | 604/366 |
| 5,342,336 | 8/1994 | Meirowitz et al. | 604/378 |
| 5,348,547 | 9/1994 | Payne et al. | 604/378 |
| 5,350,370 | 9/1994 | Jackson et al. | 604/367 |
| 5,356,405 | 10/1994 | Thompson et al. | 604/384 |
| 5,358,500 | 10/1994 | Lavon et al. | 604/385.2 |
| 5,360,420 | 11/1994 | Cook et al. | 604/378 |
| 5,364,382 | 11/1994 | Latimer et al. | 604/378 |
| 5,366,451 | 11/1994 | Levesque | 604/378 |
| 5,368,926 | 11/1994 | Thompson et al. | 428/284 |
| 5,382,245 | 1/1995 | Thompson et al. | 604/367 |
| 5,382,400 | 1/1995 | Pike et al. | 264/168 |
| 5,391,161 | 2/1995 | Hellgren et al. | 604/366 |
| 5,401,267 | 3/1995 | Couture-Dorschner | 604/384 |
| 5,418,045 | 5/1995 | Pike et al. | 428/198 |
| 5,422,169 | 6/1995 | Roe | 428/212 |
| 5,423,787 | 6/1995 | Kjellberg | 604/368 |
| 5,429,629 | 7/1995 | Latimer et al. | 604/378 |
| 5,439,458 | 8/1995 | Noel et al. | 604/378 |
| 5,454,800 | 10/1995 | Hirt et al. | 604/378 |
| 5,456,982 | 10/1995 | Hansen et al. | 428/370 |
| 5,460,622 | 10/1995 | Dragoo et al. | 604/378 |
| 5,466,410 | 11/1995 | Hills | 264/172.11 |
| 5,466,513 | 11/1995 | Wanek et al. | 428/218 |
| 5,486,166 | 1/1996 | Bishop et al. | 604/366 |
| 5,486,167 | 1/1996 | Dragoo et al. | 604/384 |
| 5,487,736 | 1/1996 | Van Phan | 604/368 |
| 5,490,846 | 2/1996 | Ellis et al. | 604/366 |
| 5,505,719 | 4/1996 | Cohen et al. | 604/372 |
| 5,509,915 | 4/1996 | Hanson et al. | 604/378 |
| 5,514,105 | 5/1996 | Goodman, Jr. et al. | 604/370 |
| 5,514,120 | 5/1996 | Johnston et al. | 604/378 |
| 5,525,407 | 6/1996 | Yang | 428/218 |
| 5,527,300 | 6/1996 | Sauer | 604/378 |
| 5,531,728 | 7/1996 | Lash | 604/378 |
| 5,536,264 | 7/1996 | Hsueh et al. | 604/368 |
| 5,540,979 | 7/1996 | Yahiaoui et al. | 428/212 |
| 5,549,589 | 8/1996 | Horney et al. | 604/366 |
| 5,556,392 | 9/1996 | Koczab | 604/378 |
| 5,562,646 | 10/1996 | Goldman et al. | 604/368 |
| 5,562,650 | 10/1996 | Everett et al. | 604/378 |
| 5,569,226 | 10/1996 | Cohen et al. | 604/378 |
| 5,599,335 | 2/1997 | Goldman et al. | 604/368 |
| 5,601,545 | 2/1997 | Glaug et al. | 604/385.2 |
| 5,607,414 | 3/1997 | Richards et al. | 604/378 |
| 5,611,981 | 3/1997 | Phillips et al. | 264/130 |
| 5,628,736 | 5/1997 | Thompson | 604/366 |
| 5,641,441 | 6/1997 | Yang | 264/113 |
| 5,643,238 | 7/1997 | Baker | 604/368 |
| 5,647,862 | 7/1997 | Osborn, III et al. | 604/378 |
| 5,649,916 | 7/1997 | DiPalma et al. | 604/378 |
| 5,658,268 | 8/1997 | Johns et al. | 604/361 |
| 5,665,082 | 9/1997 | Boulanger | 604/365 |

FOREIGN PATENT DOCUMENTS

| | | | |
|---|---|---|---|
| 0 719 530 | 7/1996 | European Pat. Off. | A61F 13/15 |
| 8164160 | 6/1996 | Japan | A61F 13/15 |
| 8164163 | 6/1996 | Japan | A61F 13/46 |
| 8299385 | 11/1996 | Japan | A61F 13/15 |
| 8317939 | 12/1996 | Japan | A61B 19/08 |
| 9000562 | 1/1997 | Japan | A61F 13/15 |
| 9117471 | 5/1997 | Japan | A61F 13/54 |
| 2 108 371 | 10/1982 | United Kingdom . | |
| 2 269 109 | 2/1994 | United Kingdom | A61F 13/15 |
| 2 280 115 | 1/1995 | United Kingdom . | |
| 2 287 041 | 9/1995 | United Kingdom . | |

| | | | | | | |
|---|---|---|---|---|---|---|
| 2 295 321 | 5/1996 | United Kingdom | A61F 13/46 | 93 01780 | 2/1993 | WIPO . |
| 2 296 511 | 7/1996 | United Kingdom . | | 93 04092 | 3/1993 | WIPO . |
| 85 03218 | 8/1985 | WIPO . | | 93 11726 | 6/1993 | WIPO . |
| 86 05661 | 9/1986 | WIPO . | | 93 11727 | 6/1993 | WIPO . |
| 90 04375 | 5/1990 | WIPO . | | 93 15702 | 8/1993 | WIPO . |
| 90/12130 | 10/1990 | WIPO | D01D 5/253 | 94 02092 | 2/1994 | WIPO . |
| 90 14061 | 11/1990 | WIPO . | | 94 23761 | 10/1994 | WIPO . |
| 90 14814 | 12/1990 | WIPO . | | 94/29506 | 12/1994 | WIPO D04H 13/00 |
| 90 14815 | 12/1990 | WIPO . | | 95/00183 | 1/1995 | WIPO A61L 15/60 |
| 91 10413 | 7/1991 | WIPO . | | 95/01147 | 1/1995 | WIPO A61F 13/15 |
| 91 10416 | 7/1991 | WIPO . | | 95 16422 | 6/1995 | WIPO . |
| 91 11161 | 8/1991 | WIPO . | | 95/25495 | 9/1995 | WIPO A61F 13/15 |
| 91 11162 | 8/1991 | WIPO . | | 95/35081 | 12/1995 | WIPO A61F 13/15 |
| 91 11163 | 8/1991 | WIPO . | | 96 01608 | 1/1996 | WIPO . |
| 91 11164 | 8/1991 | WIPO . | | 96 03947 | 2/1996 | WIPO . |
| 91 11165 | 8/1991 | WIPO . | | 96 07380 | 3/1996 | WIPO . |
| 91/11978 | 8/1991 | WIPO A61F 13/46 | | 96/12460 | 5/1996 | WIPO A61F 13/15 |
| 92 11830 | 7/1992 | WIPO . | | 96/20667 | 7/1996 | WIPO A61F 13/15 |
| 92 11831 | 7/1992 | WIPO . | | 96/41045 | 12/1996 | WIPO D04H 1/46 |
| 92 14429 | 9/1992 | WIPO . | | 97/11660 | 4/1997 | WIPO A61F 13/15 |
| 93 01778 | 2/1993 | WIPO . | | 97/13909 | 4/1997 | WIPO . |
| 93 01779 | 2/1993 | WIPO . | | 9723182 | 7/1997 | WIPO A61F 13/15 |

# MULTIFUNCTIONAL ABSORBENT MATERIAL AND PRODUCTS MADE THEREFROM

FIELD OF THE INVENTION

The present invention relates to a material structure in an absorbent article for personal care products like diapers, training pants, incontinence articles, or sanitary napkins.

BACKGROUND OF THE INVENTION

Traditional absorbent systems for personal care products store substantially all liquid insults in the crotch region. This results in the crotch region being heavily loaded with liquid by the first insult and can result in insufficient capacity for a second, third or later insult. This crotch area loading can cause the product to sag away from the wearer, causing discomfort for the wearer and creating the possibility of leakage. The storage of insults in the crotch region also requires that the crotch region be wider than would be possible in a system that stored insults in a different location. A wider crotch area also causes discomfort to the wearer. Further, storage in the crotch area does not use the entire product area for storage, resulting in waste of absorbent material which is usually spread throughout the product area. Storage primarily in the crotch area would, therefore, raise product cost through the inefficient use of materials. A system in which an insult would be accepted by a personal care product and distributed to remote areas of the product for storage away from the crotch area so that the crotch area of the product could be free to accept another insult, would be preferable to the crotch area storage design. Such a system could maximize the use of the area of the product, reduce sag and allow the production of a personal care product with a narrower, more comfortable crotch. A more efficient use of product materials may result in a lower consumer cost.

It is therefore an object of this invention to provide a multifunctional composite material to be used in liquid communication with a distribution material for urine management applications. Such a material will intake a liquid insult from the wearer, store some of it for a period of time, and release a large portion of the insult in a controlled manner to a distribution material which will move the liquid to a remote storage location. It is a further object of the invention to provide personal care products with narrow crotch designs.

SUMMARY OF THE INVENTION

A multifunctional material is provided for use in personal care products. The multifunctional material has a permeability between about 100 and 10000 Darcys, a capillary tension between about 2 and 15 cm. Structures comprising this multifunctional material can have a runoff rate of less than 25 ml per 100 ml insult, over its life. The multifunctional material should have between about 30 and 75 weight percent of a superabsorbent, between 25 and 70 weight percent of pulp and from a positive amount up to about 10 percent of a binder component. The material preferably has a density between about 0.05 and 0.5 g/cc. The material has a liquid pass through function which accepts liquid during insults and then desorbs a surge material across time frames consistent with user conditions and releases the liquid for distribution to remote storage locations. The material, when combined with the intake and distribution materials, defines a composite structure for use in personal care products. Personal care products using this material may have a narrower crotch than previous products because of the superior performance of the material.

DEFINITIONS

Figure 1:
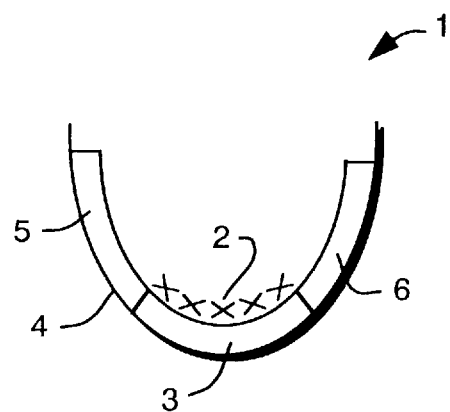
FIG. 1 is a cross-sectional side view of a diaper incorporating the multifunctional material of this invention.

"Disposable" includes being disposed of after use and not intended to be washed and reused.

"Front" and "back" are used throughout this description to designate relationships relative to the garment itself, rather than to suggest any position the garment assumes when it is positioned on a wearer.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

"Inward" and "outward" refer to positions relative to the center of an absorbent garment, and particularly transversely and/or longitudinally closer to or away from the longitudinal and transverse center of the absorbent garment.

"Layer" when used in the singular can have the dual meaning of a single element or a plurality of elements.

"Liquid" means a substance and/or material that flows and can assume the interior shape of a container into which it is poured or placed.

"Liquid communication" means that liquid such as urine is able to travel from one layer to another layer.

"Longitudinal" and "transverse" have their customary meaning, as indicated by transverse section line x—x in Fig.

x. The longitudinal axis lies in the plane of the article when laid flat and fully extended and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Particles" refers to any geometric form such as, but not limited to, spherical grains, cylindrical fibers or strands, flat surfaces or roughened surfaces, sheets, ribbons, strings, strands, or the like.

"Spray" and variations thereof include forcefully ejecting liquid, either as a stream or, such as swirl filaments, or atomized particles through an orifice, nozzle, or the like, by means of an applied pressure of air or other gas, by force of gravity, or by centrifugal force. The spray can be continuous or non-continuous.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 30 microns. The fibers may also have shapes such as those described in U.S. Pat. No. 5,277,976 to Hogle et al., U.S. Pat. Nos. 5,466,410 to Hills and 5,069,970 and 5,057,368 to Largman et al., which describe fibers with unconventional shapes.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

"Conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al., and 5,069,970 and 5,057,368 to Largman et al., hereby incorporated by reference in their entirety, which describe fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

"Bonded carded web" refers to webs which are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

"Personal care product" means diapers, training pants, absorbent underpants, adult incontinence products, and feminine hygiene products.

TEST METHODS

Absorption Time Index (ATI): In this test the absorbent capacity of a superabsorbent material is determined versus time for up to 200 minutes under light pressure, e.g. about 0.01 psi.

A one inch (25.4 mm) inside diameter cylinder with an integral 100 mesh stainless steel screen on one end is used to hold 0.16±0.005 grams of dry superabsorbent. The superabsorbent should be carefully placed in the cylinder so that superabsorbent does not stick to the sides of the cylinder. The cylinder should be tapped gently to more evenly distribute the superabsorbent on the screen. A 4.4 gram, 0.995 inch (252.73 mm) diameter plastic piston is then placed in the cylinder and the cylinder, piston and superabsorbent assembly weighed. The assembly is placed in a 3 inch by 3 inch (76.4 mm by 76.4 mm) liquid basin having a 0.875 weight percent NaCl saline solution to a depth of 1 cm. Tap the cylinder gently to remove any air trapped under it and maintain the saline solution depth at 1 cm throughout the test.

Use a timer capable of reading 200 minutes in one second intervals. Start the timer and after 5 minutes in the solution, remove the assembly and blot on absorbent paper. A preferred paper is Kleenex® Premium Dinner Napkins from Kimberly-Clark Corp. though any other effective paper may be used. In blotting, press the paper tightly against the cylinder to ensure good contact. Touch the cylinder three times to dry paper and there should be very little liquid removed the third time. Weigh the assembly and return assembly to the liquid basin. Blotting and weighing should take about 5 seconds and the timer should be kept running throughout the test. Take readings at 5, 10, 15, 30, 45, 60, 75, 90, 120, 160 and 200 minutes. Use fresh dry napkins for each reading.

After the final reading, calculate the grams of liquid absorbed per gram of superabsorbent. The amount of liquid absorbed at particular times divided by the amount absorbed at 200 minutes may be plotted versus time for a graphical representation of the absorption rate.

The ATI is calculated as follows:

$$ATI=(t_{10}+t_{20}+t_{30}+t_{40}+t_{50}+t_{60}+t_{70}+t_{80}+t_{90})/9$$

where $t_n$ is the time in minutes at which n percentage of the absorbent capacity at 200 minutes is used, e.g. $t_{30}$ is the time at which 30 percent of the total capacity is used.

Absorption under tension (AUT) test: This test is a modified version of TAPPI method T561 pm-96 which is entitled "sorptive rate and capacity of bibulous paper products using gravimetric principles". Appendix A2 of TAPPI method T561pm-96 discusses nonstandard variations.

A specimen of the sample is place on a horizontal test plate such that its bottom surface rests on the plate and its upper surface is covered by a test weight. The sample is surrounded by a restraint such that it may only expand in one direction; the direction covered by the weight. The test plate is connected to a liquid reservoir by means of a siphon tube. The specimen is in contact with the effluent (8.5 g/l saline solution) of the siphon tube and the top surface of the liquid reservoir in relation to the sample may be adjusted during the test. The liquid reservoir is placed on a suitable weighing device. During the test, liquid is absorbed into the specimen and this absorption causes a reduction in the liquid present in the liquid reservoir which is measured by the weighing device. The decrease in weight in the liquid reservoir may be plotted directly or divided by the grams of the sample to provide an absorbent capacity per gram of sample over time.

In the test procedure used herein the sample was 6.25 cm (2.75 inches) in diameter and the sample height and weight were dependent on sample density. The sample was surrounded by a 6.25 cm diameter round glass ring to restrict expansion horizontally. The test weight was 674.14 gms in order to maintain a pressure of about 0.25 psi on the sample. The difference in height between the surface of the liquid reservoir and the sample was maintained at zero centimeters.

Figure 2:
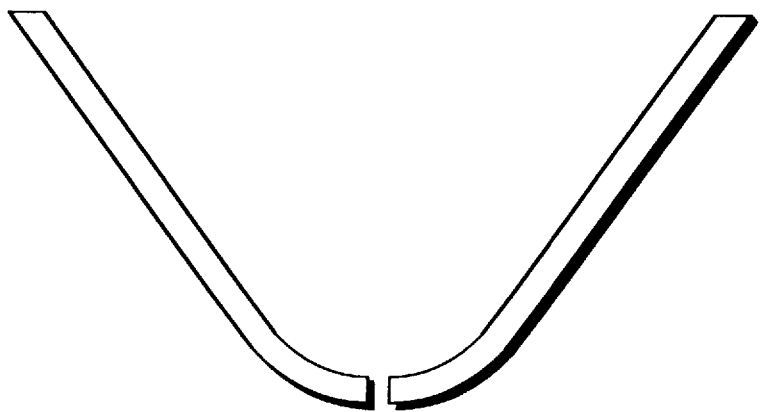
FIG. 2 is a drawing of a side view of a cradle used for the MIST Evaluation test.

Multiple Insult Test (MIST Evaluation): In this test a fabric, material or structure composed of two or more materials is placed in an acrylic cradle to simulate body curvature of a user such as an infant. Such a cradle is illustrated in FIG. 2. The cradle has a width into the page of the drawing as shown of 33 cm and the ends are blocked off, a height of 19 cm, an inner distance between the upper arms of 30.5 cm and an angle between the upper arms of 60 degrees. The cradle has a 6.5 mm wide slot at the lowest point running the length of the cradle into the page.

The material to be tested is placed on a piece of polyethylene film the same size as the sample and placed in the cradle. The material to be tested is insulted with 100 ml of a saline solution of 8.5 grams of sodium chloride per liter, at a rate of 20 cc/sec with a nozzle normal to the center of the material and 14 inch (6.4 mm) above the material. The amount of runoff is recorded. The material is immediately removed from the cradle, weighed, and placed on a dry 40/60 pulp/superabsorbent pad having a density of 0.2 g/cc in a horizontal position under 0.01 psi pressure and weighed after 5, 15 and 30 minutes to determine liquid desorption from the material into the superabsorbent pad as well as liquid retention in the material. The pulp fluff and superabsorbent used in this test is Kimberly-Clark's (Dallas Tex.) CR-2054 pulp and Stockhausen Company's (of Greensboro, N.C. 27406) FAVOR 870 superabsorbent though other comparable pulp and superabsorbents could be used provided they yield a desorption pad of 500 gsm and 0.2 g/cc which after immersion into saline solution under free-swell conditions for 5 minutes, retains at least 20 grams of saline solution per gram of desorption pad after being subjected to an air pressure differential, by vacuum suction for example, of about 0.5 psi (about 3.45 kPa) applied across the thickness of the pad for 5 minutes. If the tested piece is made of other components (e.g. is a laminate) the components or layers are separated and weighed to determine liquid partitioning between them and then reassembled after each weighing and placed back onto the fluff/superabsorbent. This test is repeated using fresh desorption pads on each insult so that a total of three insults are introduced and liquid partitioning measured over 1.5 hours with 30 minutes between insults. Five tests of each sample material are recommended.

X-ray imaging test: This test was one method used to determine the amount of liquid in each of the five zones of the absorbent systems. X-ray imaging is known in the art as discussed, for example, in an article entitled "Liquid Distribution: comparison of X-ray Imaging Data" by David F. Ring, Oscar Lijap and Joseph Pascente in *Nonwovens World* magazine, summer 1995, at pages 65–70. Generally, this procedure compares x-ray images of a wet and dry sample in order to calculate the liquid content. Such x-ray systems are available from Tronix Inc. of 31 Business Park Drive, Branford, Conn. 06045 as model no. 10561 HF 100 w/enclosure. This system uses software from Optumus Inc., of Ft. Collins, Colo. as Bio-scan Optimate® S/N OPM4101105461 version 4.11.

Capillary Tension: The capillary tension (c.t.) expressed in centimeters (cm) of the liquid is calculated from fiber and web characteristics by equating the capillary pressure exerted by the material to the hydrostatic pressure provided by a column of liquid by a method known in the art and taught in a number of references, for example *Textile Science and Technology*, vol. 7, by Pronoy K. Chatterjee, published by Elsevier Science Publishers B.V. 1985, ISBN 0-444-42377-X (vol. 7), chapters 2,4,5. These calculations assume a surface tension of 68 dynes/cm which is taken from a 8.5 gm/l saline solution used as an approximation or simulation of urine. Urine can be quite variable in surface tension.

Capillary tension can be computed or determined experimentally by vertical wicking height testing described herein. Computations are utilized in the presence of test liquids, especially materials containing superabsorbents when exposed to saline.

| Variable | | Dimensions |
|---|---|---|
| $c.t. = \dfrac{2}{\sqrt{\pi}} \dfrac{\gamma}{\left(\dfrac{1}{\rho_{web}} - \dfrac{1}{\rho_{avg}}\right)} \dfrac{\alpha}{980}$ | | cm saline |
| $\alpha = \sum\limits_i \dfrac{x_i}{r_{i,eff}\rho_i} \cos(\theta)$ | | cm²/g |
| $\rho_{avg} = \left(\sum\limits_i \dfrac{x_i}{\rho_i}\right)^{-1}$ | | g/cm³ |
| $\rho_{web} = \dfrac{BW}{10^3 t}$ | | g/cm³ |
| $r_{i,eff} = \dfrac{V_i}{SA_i}$ | | cm |
| for long cylinders $r_{i,eff}$(cm) = | $\dfrac{\dfrac{\pi d_i^2 L}{4}}{\pi d_i L} = \dfrac{d_i}{4 \times 10^4}$ | |
| for spheres $r_{i,eff}$(cm) = | $\dfrac{\dfrac{4}{3} \dfrac{\pi d_i^3}{8}}{\pi d_i^2} = \dfrac{d_i}{6 \times 10^4}$ | | where $\gamma$=surface tension of liquid (dyne/cm)

$\theta_i$=advancing liquid-solid contact angle (degrees) for component i $\pi$=3.1415906

$\rho_{web}$=density of web (g/cm³)

$\rho_{avg}$=mass weighted average component density (g/cm³)

$d_i$=diameter of component i (microns)

$\rho_i$=density of component i (g/cm³)

$x_i$=mass fraction of component i in web $r_{i,eff}$=effective fiber radius (cm)

BW=weight of sample/area (g/m²)

t=thickness of sample (mm) under 0.05 psi (23.9 dyne/cm²) or 2.39 Pascal (N/m²) load L=cylinder length (cm)

$V_i$=volume of component i (cm³)

$SA_i$=surface area of component i (cm²)

Capillary Tension Example Calculation

For a structure which contains 57% southern softwood pulp, 40% superabsorbent and 3% binder fiber, and has a basis weight of 617.58 g/m² and a bulk thickness of 5.97 mm at 0.05 psi, the example calculation of capillary tension of saline follows. The component properties are as follows:

| Component | Shape | Diameter $d_i$ (microns) | Contact Angle $\theta_i$ | Density $\rho_i$ (g/cm³) | Mass Fraction $x_i$ |
|---|---|---|---|---|---|
| So. Softwood | Cylinder | 13.3 | 45 | 1.55 | 0.57 |
| Super-absorbent | Sphere | 1125 | 30 | 1.49 | 0.40 |
| Binder fiber | Cylinder | 17.5 | 90 | 0.91 | 0.03 |

Note that the shape and contact angles are approximated.

| Variable | | |
|---|---|---|
| $\alpha$(cm²/g) | = | $\sum\limits_i \dfrac{x_i}{r_{i,eff}\rho_i} \cos(\theta)$ |
| $\alpha$(cm²/g) | = | $\dfrac{0.57\cos(45)}{\left(\dfrac{13.3}{4 \times 10^4}\right) \times 1.55} + \dfrac{0.40\cos(30)}{\left(\dfrac{1125}{6 \times 10^4}\right) \times 1.49} + \dfrac{0.03\cos(90)}{\left(\dfrac{17.5}{4 \times 10^4}\right) \times 0.925}$ |
| $\alpha$(cm²/g) | = | 794.5 |
| $\rho_{avg}$(g/cm³) | = | $\left(\sum\limits_i \dfrac{x_i}{\rho_i}\right)^{-1}$ |
| $\rho_{avg}$(g/cm³) | = | $\left(\dfrac{0.57}{1.55} + \dfrac{0.40}{1.49} + \dfrac{0.03}{0.925}\right)^{-1}$ |
| $\rho_{avg}$(g/cm³) | = | 1.496 |
| $\rho_{web}$(g/cm³) | = | $\dfrac{BW}{10^3 t}$ |
| $\rho_{web}$(g/cm³) | = | $\dfrac{617.58}{(5.97)10^3}$ |
| $\rho_{web}$(g/cm³) | = | 0.1034 |
| $c.t.$(cm saline) | = | $\dfrac{2}{\sqrt{\pi}} \dfrac{\gamma}{\left(\dfrac{1}{\rho_{web}} - \dfrac{1}{\rho_{avg}}\right)} \dfrac{\alpha}{980}$ |
| $c.t.$(cm saline) | = | $\dfrac{2}{\sqrt{\pi}} \dfrac{68}{\left(\dfrac{1}{0.1034} - \dfrac{1}{1.496}\right)} \dfrac{794.5}{980}$ |
| $c.t.$(cm saline) | = | 6.91 |

Permeability: Permeability (k) may be calculated from the Kozeny-Carman equation. This is a widely used method. References include an article by R. W. Hoyland and R. Field in the journal *Paper Technology and Industry*, December 1976, p. 291–299 and *Porous Media Liquid Transport and Pore Structure* by F. A. L. Dullien, 1979, Academic Press, Inc. ISBN 0-12-223650-5.

| | Calculated Variable | Equation | Dimensions |
|---|---|---|---|
| Permeability = | k = | $\dfrac{\epsilon^3}{KS_0^2(1-\epsilon)^2} \dfrac{1}{9.87 \times 10^{-9}}$ | Darcys |
| Kozeny Constant = | K = | $\dfrac{3.5\epsilon^3}{(1-\epsilon)^{0.5}} [1 + 57(1-\epsilon)^3]$ | dimensionless |

-continued

| Calculated Variable | | Equation | Dimensions |
|---|---|---|---|
| Surface area per mass of the material | $S_v =$ | $\sum_i \dfrac{x_i}{r_{i,\mathit{eff}}\rho_i}$ | cm²/g |
| Mass weighted average component density | $\rho_{avg} =$ | $\left(\sum_i \dfrac{x_i}{\rho_i}\right)^{-1}$ | g/cm³ |
| Surface area per solid volume of the material | $S_0 =$ | $S_v\rho_{avg}$ | cm⁻¹ |
| Porosity | $\epsilon =$ | $1 - \sum_i x_i \dfrac{\rho_{web}}{\rho_i}$ | dimensionless |
| Effective fiber radius | $r_{i,\mathit{eff}} =$ | $\dfrac{V_i}{SA_i}$ | cm |
| Density of web | $\rho_{web} =$ | $\dfrac{BW}{10^3 \cdot t}$ | g/cm³ |
| for long cylinders | $r_{i,\mathit{eff}} =$ | $\dfrac{\dfrac{\pi d_i^2 L}{4}}{\pi d_i L} = \dfrac{d_i}{4 \times 10^4}$ | |
| for spheres | $r_{i,\mathit{eff}} =$ | $\dfrac{\dfrac{4}{3}\dfrac{\pi d_i^3}{8}}{\pi d_i^2} = \dfrac{d_i}{6 \times 10^4}$ | | where $d_i$=diameter of component i (microns)
$\rho_i$=density of component i (g/cm³)
$x_i$=mass fraction of component i in web
BW=weight of sample/area (g/m²)
t=thickness of sample (mm) under 0.05 psi (23.9 dyne/cm²) or 2.39 Pascal (N/m²) load Permeability Example Calculation For a structure which contains 57% southern softwood pulp, 40% superabsorbent and 3% binder fiber, and has a basis weight of 617.58 g/m² and a bulk thickness of 5.97 mm at 0.05 psi the example permeability calculation follows. The component properties are as follows (note shape is approximated):

| Component | Shape | Diameter $d_i$ (microns) | Density $\rho_i$ (g/cm³) | Mass Fraction $x_i$ |
|---|---|---|---|---|
| Southern softwood | Cylinder | 13.3 | 1.55 | 0.57 |
| Superabsorbent | Sphere | 1125 | 1.50 | 0.40 |
| Binder | Cylinder | 17.5 | 0.925 | 0.03 |

$\rho_{web}(\text{g/cm}^3) = \dfrac{BW}{10^3 \cdot t}$ $\rho_{web}(\text{g/cm}^3) = \dfrac{617.58}{(5.97)10^3}$ $\rho_{web}(\text{g/cm}^3) = 0.1034$ $\epsilon = 1 - \sum_i x_i \dfrac{\rho_{web}}{\rho_i}$ $\epsilon = 1 - 0.57\dfrac{0.1034}{1.55} - 0.40\dfrac{0.1034}{1.49} - 0.03\dfrac{0.1034}{0.925}$ -continued

| Component | Shape | Diameter $d_i$ (microns) | Density $\rho_i$ (g/cm³) | Mass Fraction $x_i$ |
|---|---|---|---|---|

$S_v(\text{cm}^2/\text{g}) = \sum_i \dfrac{x_i}{r_{i,\mathit{eff}}\rho_i}$ $S_v(\text{cm}^2/\text{g}) =$ $\dfrac{0.57}{\left(\dfrac{13.3}{4 \times 10^4}\right) \times 1.55} + \dfrac{0.40}{\left(\dfrac{1125}{6 \times 10^4}\right) \times 1.49} + \dfrac{0.03}{\left(\dfrac{17.5}{4 \times 10^4}\right) \times 0.925}$ $S_v(\text{cm}^2/\text{g}) = 1194$ $\rho_{avg}(\text{g/cm}^3) = \left(\sum_i \dfrac{x_i}{\rho_i}\right)^{-1}$ $\rho_{avg}(\text{g/cm}^3) = \left(\dfrac{0.57}{1.55} + \dfrac{0.40}{1.49} + \dfrac{0.03}{0.925}\right)^{-1}$ $\rho_{avg}(\text{g/cm}^3) = 1.496$
$S_0(\text{cm}^{-1}) = S_v\rho_{avg}$
$S_0(\text{cm}^{-1}) = 1194 \times 1.496$
$S_0(\text{cm}^{-1}) = 1786$ $K = \dfrac{3.5\epsilon^3}{(1-\epsilon)^{0.5}}[1 + 57(1-\epsilon)^3]$ $K = \dfrac{3.5(0.9309)^3}{(1-0.9309)^{0.5}}[1 + 57(1-0.9309)^3]$ $K = 10.94$ $k = \dfrac{\epsilon^3}{KS_0^2(1-\epsilon)^2} \dfrac{1}{9.87 \times 10^{-9}}$ -continued

| Component | Shape | Diameter $d_i$ (microns) | Density $\rho_i$ (g/cm³) | Mass Fraction $x_i$ |
|---|---|---|---|---|

$$k = \frac{(0.9309)^3}{(10.94)(1786)^2(1-0.9309)^2} \quad \frac{1}{9.87 \times 10^{-9}}$$

$k = 491$ darcys

Material caliper (thickness) The caliper of a material is a measure of thickness and is measured at 0.05 psi with a Starret-type bulk tester, in units of millimeters.

Density The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (g/cc). A total of three samples would be evaluated and averaged for the density values.

Wicking Time and Vertical Liquid Flux of an Absorbent Structure A sample strip of material approximately 2 inches (5 cm) by 15 inches (38 cm) is placed vertically such that when the sample strip is positioned above a liquid reservoir at the beginning of the test, the bottom of the sample strip will just touch the liquid surface. The liquid used was a 8.5 g/l saline solution. The relative humidity should be maintained at about 90 to about 98 percent during the evaluation. The sample strip is placed above the known weight and volume of liquid and a stopwatch started as soon as the bottom edge of the sample strip touches the surface of the solution.

The vertical distance of the liquid front traveling up the sample strip and the liquid weight absorbed by the sample strip at various times is recorded. The time versus liquid front height is plotted to determine the Wicking Time at about 5 centimeters and at about 15 centimeters. The weight of the liquid absorbed by the sample strip from the beginning of the evaluation to about 5 centimeters and to about 15 centimeters height is also determined from the data. The Vertical Liquid Flux value of the sample strip at a particular height was calculated by dividing the grams of liquid absorbed by the sample strip by each of: the basis weight (gsm), of the sample strip; the time, in minutes, needed by the liquid to reach the particular height; and the width, in inches, of the sample strip. Capillary tension in materials not containing superabsorbents (e.g. surge materials) is measured simply by the equilibrium vertical wicking height of a 8.5 g/l saline solution after 30 minutes.

DETAILED DESCRIPTION OF THE INVENTION

Previous attempts to improve the effectiveness of disposable personal care products have included distributing the particles of fluff or super absorbent material (SAM) in particular areas of the article or providing differently shaped storage or holding areas into which insults are absorbed prior to absorption by the absorbent core. Such methods do not generally utilize the entire available interior surface of the product or do not use it to the same degree, therefore resulting in inefficient usage of the body of the product article.

Prior attempts also resulted in structures in which much of the liquid to be absorbed remains in the crotch area of the article. A structure so designed must be quite wide in the crotch and therefore uncomfortable for the wearer, particularly after the absorbing of liquid by the absorbent core and subsequent swelling of the absorbent material. Storage in the crotch also increases the tendency of the product to sag away from the wearer's body.

A need remains therefore, for a disposable personal care product in which a large portion of the available area of the article is used for absorbency of body liquid insults and which does not retain the bulk of the insult in the crotch area. This would allow for narrower crotch, more body-conforming articles to be produced and so result in better fit and greater comfort of the wearer, and more efficient usage of materials. When referring to diapers and training pants, a narrow crotch is one which is at most 7.6 cm in width, more particularly, at most 5 cm in width.

Traditional absorbent systems for personal care products may be generalized as having the functions of Intake (surge control) and containment (retention) or SC.

Surge control materials, the "S" in SC, are provided to quickly accept the incoming insult that it does not leak outside the article. The surge layer may also be referred to as an intake layer, transfer layer, transport layer and the like. A surge material must typically be capable of handling an incoming insult of between about 60 and 100 cc at a volumetric flow rate of from about 5 to 20 cc/sec, for infants, for example.

Containment or retention materials, the "C" in SC, must absorb the insult quickly and efficiently. They should be capable of absorbing the liquid without significant "gel blocking" or blocking of penetration of liquid further into the absorbent by the expansion of the outer layers of absorbent. Retention materials are often high rate superabsorbent materials such as blends of polyacrylate superabsorbent and fluff. These materials rapidly absorb and hold liquid. Examples of retention materials may be found in U.S. Pat. No. 5,350,370 to Jackson et al., commonly assigned.

As mentioned above, traditional absorbent systems having the functions of intake and containment usually hold the vast majority of any insult in the target area, usually the crotch. Liquid is moved away from the crotch in such systems only after the crotch capacity is filled. This results in personal care products having crotches which are quite wide. Examples of the holding ability and location of containment of various commercial diapers is presented in Table 3 of U.S. patent Ser. No. 08/755,136, filed the same day and assigned to the same assignee as this application and entitled ABSORBENT ARTICLES WITH CONTROLLABLE FILL PATTERNS.

In contrast with traditional absorbent systems, the patent application ABSORBENT ARTICLES WITH CONTROLLABLE FILL PATTERNS presents an absorbent system which includes components that have been designed, arranged, and assembled so that within a certain time after each insult, liquid will be located in a pre-specified area of the absorbent system, i.e. remote from the target area. Using an absorbent system arbitrarily divided into five zones, these absorbent systems have a "fill ratio" of grams of liquid located in the center target zone, usually in the crotch, to each of the two end zones which is less than 5:1 after three insults of 100 ml separated by 30 minutes. It is preferred that this fill ratio be less than 3:1, and most preferred to be less than 2.5:1. Many currently available commercial diapers have fill ratios of 20:1, 50:1 or even greater, i.e. they hold most insult liquid in the crotch.

In addition to the surge control and containment materials in traditional absorbent systems, recent work has introduced another component interposed between the S and C layers. This new component is a distribution material, producing a system with surge control, distribution and containment or "SDC".

Distribution materials, the "D" in SDC, must be capable of moving liquid from the point of initial deposition to where storage is desired. Distribution must take place at an acceptable rate such that the target insult area, generally the crotch area, is ready for the next insult. By "ready for the next insult" it is meant that sufficient liquid has been moved out of the target zone so that the next insult results in liquid absorption and runoff within acceptable volumes. The time between insults can range from just a few minutes to hours, generally depending on the age of the wearer.

The multifunctional material of this invention is located between the surge material and the distribution material as shown in FIG. 1 which is a cross-sectional view of a personal care product, in this case a diaper. The diaper 1 has surge material 2 in the intake area, the multifunctional material 3 below the surge material 2, distribution material 4 below the multifunctional material 3 and retention/storage material 5, 6 at either end of the diaper 1. Such products also usually have a liner material and backsheet (not shown for clarity). While it may appear obvious, it should be noted that in order to function effectively, the materials used in this invention must have sufficient contact to transfer liquid between them.

The liner is sometimes referred to as a bodyside liner or topsheet and is adjacent to the surge material. The liner material is the layer against the wearer's skin and so the first layer in contact with liquid or other exudate from the wearer. The liner further serves to isolate the wearer's skin from the liquids held in an absorbent structure and should be compliant, soft feeling and non-irritating.

Various materials can be used in forming the bodyside liner of the present invention, including apertured plastic films, woven fabrics, nonwoven webs, porous foams, reticulated foams and the like. Nonwoven materials have been found particularly suitable for use in forming the bodyside liner, including spunbond or meltblown webs of polyolefin, polyester, polyamide (or other like fiber forming polymer) filaments, or bonded carded webs of natural polymers (for example, rayon or cotton fibers) and/or synthetic polymers (for example, polypropylene or polyester) fibers. For example, the bodyside liner can be a nonwoven spunbond web of synthetic polypropylene filaments. The nonwoven web can have a basis weight ranging from about 10.0 grams per square meter (gsm) to about 68.0 gsm, and more particularly from about 14.0 gsm to about 42.0 gsm, a bulk or thickness ranging from about 0.13 millimeter (mm) to about 1.0 mm, and more particularly from about 0.18 mm to about 0.55 mm, and a density between about 0.025 grams per cubic centimeter (g/cc) and about 0.12 g/cc, and more particularly between about 0.068 g/cc and about 0.083 g/cc. Additionally, the permeability of such nonwoven web can be from about 150 Darcy to about 5000 Darcy. The nonwoven web can be surface treated with a selected amount of surfactant, such as about 0.28% Triton X-102 surfactant, or otherwise processed to impart the desired level of wettability and hydrophilicity. If a surfactant is used, it can be applied to the web by any conventional means, such as spraying, printing, brush coating and the like.

The surge layer is most typically interposed between and in intimate, liquid communicating contact with the bodyside liner and another layer such as a distribution or retention layer, although in this invention it is in contact with the multifunctional material of this invention. The surge layer is usually subjacent the inner (unexposed) surface of bodyside liner. To further enhance liquid transfer, it can be desirable to attach the upper and/or lower surfaces of the surge layer to the liner and the distribution layer, respectively. Suitable conventional attachment techniques may be utilized, including without limitation, adhesive bonding (using water-based, solvent-based and thermally activated adhesives), thermal bonding, ultrasonic bonding, needling and pin aperturing, as well as combinations of the foregoing or other appropriate attachment methods. If, for example, the surge layer is adhesively bonded to the bodyside liner, the amount of adhesive add-on should be sufficient to provide the desired level(s) of bonding, without excessively restricting the flow of liquid from the liner into the surge layer. One exemplary surge material may be found in U.S. patent Ser. No. 08/756,514, filed the same day and assigned to the same assignee as this application and entitled HIGHLY EFFICIENT SURGE MATERIAL FOR ABSORBENT ARTICLES which presents a surge material which is a web of wettable fibers of 30 microns in diameter or less which is substantially uniform and where the web has a permeability of between about 250 and 1500 Darcys and a capillary tension between 1.5 and 5 cm.

Various woven fabrics and nonwoven webs can be used to construct a surge layer. For example, the surge layer may be a nonwoven fabric layer composed of a meltblown or spunbond web of polyolefin filaments. Such nonwoven fabric layers may include conjugate, biconstituent and homopolymer fibers of staple or other lengths and mixtures of such fibers with other types of fibers. The surge layer also can be a bonded carded web or an airlaid web composed of natural and/or synthetic fibers. The bonded carded web may, for example, be a powder bonded carded web, an infrared bonded carded web, or a through-air bonded carded web. The bonded carded webs can optionally include a mixture or blend of different fibers, and the fiber lengths within a selected web may range from about 3 mm to about 60 mm. Exemplary surge layers can have a basis weight of at least about 0.50 ounce per square yard (about 17 grams per square meter), a density of at least about 0.010 gram per cubic centimeter at a pressure of 68.9 Pascals, a bulk of at least about 1.0 mm at a pressure of 68.9 Pascals, a bulk recovery of at least about 75 percent, a permeability of about 500 to about 5000 Darcy, and a surface area per void volume of at least about 20 square centimeters per cubic centimeter. The surge layer may be composed of a substantially hydrophobic material, and the hydrophobic material may optionally be treated with a surfactant or otherwise processed to impart a desired level of wettability and hydrophilicity. The surge layer can have a generally uniform thickness and cross-sectional area.

The distribution layer must be capable of moving liquid from the point of initial deposition to where storage is desired. Distribution must take place at an acceptable rate such that the target insult area, generally the crotch area, is ready for the next insult. The time between insults can range from just a few minutes to hours, generally depending on the age of the wearer. In order to achieve this transportation function, a distribution layer must have a high capillary tension value. Capillary tension in distribution and other materials not containing superabsorbents is measured simply by the equilibrium vertical wicking height of a 8.5 g/l saline solution according to the Vertical Liquid Flux rate test, not by the test method given for materials containing superabsorbents. A successful distribution layer must have a capillary tension greater than the adjacent material from which it receives liquid (on the side toward the wearer) and preferably a capillary tension of at least about 15 cm. Because of the generally inverse relationship between capillary tension and permeability, such a high capillary tension indicates that the distribution layer will usually have a low permeability.

Another liquid transport property desired of a suitable distribution material is that it exhibit a Vertical Liquid Flux rate, at a height of about 15 centimeters, suitably of at least about 0.002 grams of liquid per minute per square meter (gsm) of distribution material per inch of cross-sectional width of the distribution material g/(min*gsm*inch), up to about 0.1 g/(min*gsm*inch). As used herein, the Vertical Liquid Flux rate value of a distribution material is meant to represent the amount of liquid transported across a boundary a specified vertical distance away from a centralized liquid insult location per minute per normalized quantity of the distribution material. The Vertical Liquid Flux rate, at a height of about 15 centimeters, of a distribution may be measured according to the test method described herein.

Another liquid transport property desired of a distribution material is that it exhibit a Vertical Liquid Flux rate, at a height of about 5 centimeters, suitably of at least about 0.01 g/(min*gsm*inch) up to about 0.5 g/(min*gsm*inch). The Vertical Liquid Flux rate, at a height of about 5 centimeters, of an absorbent structure may be measured according to the test method described herein.

Materials from which the distribution layer may be made include woven fabrics and nonwoven webs, foams and filamentious materials. For example, the distribution layer may be a nonwoven fabric layer composed of a meltblown or spunbond web of polyolefin, polyester, polyamide (or other web forming polymer) filaments. Such nonwoven fabric layers may include conjugate, biconstituent and homopolymer fibers of staple or other lengths and mixtures of such fibers with other types of fibers. The distribution layer also can be a bonded carded web, an airlaid web or a wetlaid pulp structure composed of natural and/or synthetic fibers, or a combination thereof. The distribution layer may have a basis weight of from 35 to 300 gsm, or more preferably from 80 to 200 gsm, a density of between about 0.08 and 0.5 g/cc and a permeability between about 50 and 1000 Darcys.

The backsheet is sometimes referred to as the outer cover and is located the farthest layer from the wearer. The outer cover is typically formed of a thin thermoplastic film, such as polyethylene film, which is substantially impermeable to liquid. The outer cover functions to prevent body exudates contained in an absorbent structure from wetting or soiling the wearer's clothing, bedding, or other materials contacting the diaper. The outer cover may be, for example, a polyethylene film having an initial thickness of from about 0.5 mil (0.012 millimeter) to about 5.0 mil (0.12 millimeter). The polymer film outer cover may be embossed and/or matte finished to provide a more aesthetically pleasing appearance. Other alternative constructions for outer cover include woven or nonwoven fibrous webs that have been constructed or treated to impart the desired level of liquid impermeability, or laminates formed of a woven or nonwoven fabric and thermoplastic film. The outer cover may optionally be composed of a vapor or gas permeable, microporous "breathable" material, that is permeable to vapors or gas yet substantially impermeable to liquid. Breathability can be imparted in polymer films by, for example, using fillers in the film polymer formulation, extruding the filler/polymer formulation into a film and then stretching the film sufficiently to create voids around the filler particles, thereby making the film breathable. Generally, the more filler used and the higher the degree of stretching, the greater the degree of breathability.

The multifunctional material of this invention is located adjacent to the surge material and between the surge material and the distribution material and accepts and holds much of the liquid from an insult until the distribution material can move the liquid out of the intake zone. The basic structure of the multifunctional material of this invention is a unique combination of superabsorbent material, preferably slow rate superabsorbent, with high bulk, wet resilient pulp, and a structure stabilizing component such as a polyolefin binder fiber in a composite structure.

By "slow rate" superabsorbent what is meant is a superabsorbent having an absorption time index (ATI) of at least 5 minutes and preferably more than 10 minutes. Adjusting the rate of absorbency of a superabsorbent may be achieved by modifications to the particle size, surface properties, and chemistry of the polymer. Note that although slow rate superabsorbents are preferred and are referred to herein, a blend of slow rate and conventional superabsorbents may be used as well, provided the permeability and capillary tension of the multifunctional material are within the required ranges as set forth herein.

The multifunctional material has been designed to assist the surge material 1) by accepting a portion of the insult volume during forced flow, i.e. during an actual insult, 2) by desorbing the surge material of liquid during and after insults, 3) by allowing a portion of the insult volume to pass through itself (the multifunctional material) during insult to the distribution material and 4) by permanently absorbing a portion of the liquid insult. The multifunctional material must perform these functions despite actual use pressures and despite gravity effects caused by movement of the wearer.

During and after an insult, the multifunctional material described herein accepts the excess liquid retained in the surge material and releases a defined portion of liquid to the distribution material for movement to final storage locations. The multifunctional material provides permanent storage for a portion of the liquid, but product fit and bulk advantages will be achieved if only a relatively small portion of the liquid is ultimately stored in the multifunctional material in the target insult area. Product performance improvements will be achieved if that liquid stored in the multifunctional material in the target insult zone does not detract from the other three functions provided by the multifunctional material. All of these functions must continue across multiple insults, requiring a regeneration of internal void volume in the multifunctional material while maintaining appropriate interactions with the intake and distribution materials.

Figure 3:
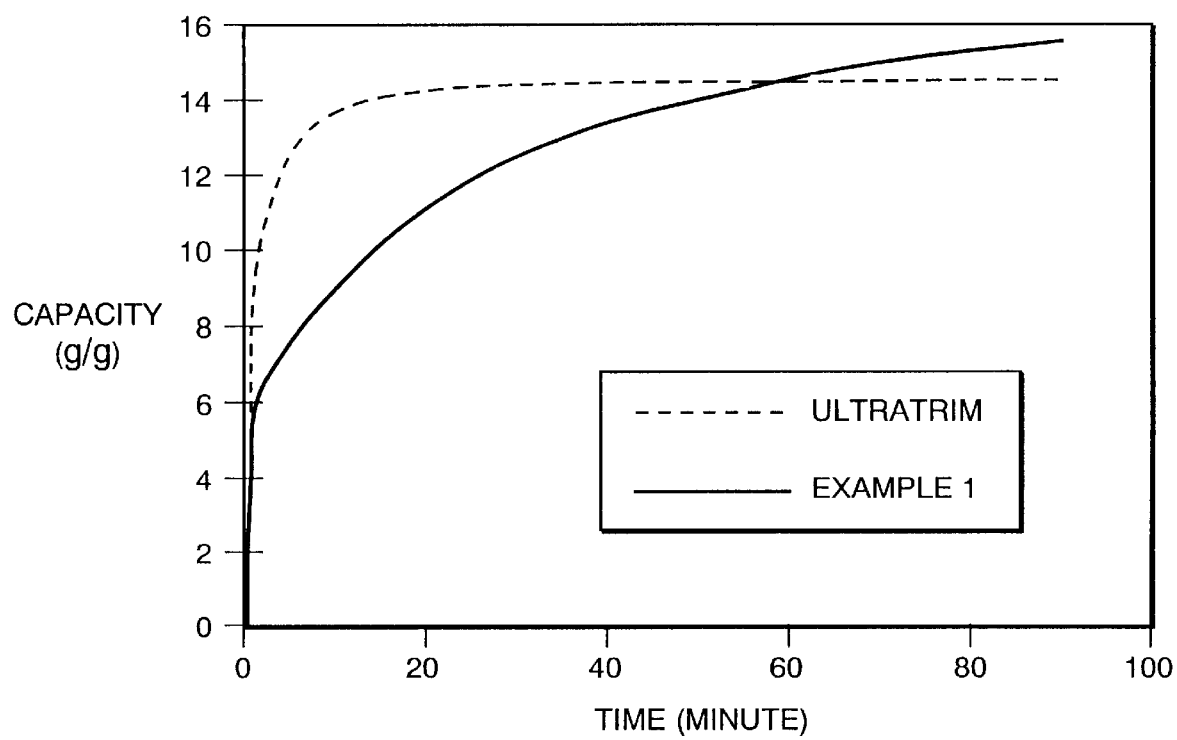
FIG. 3 is a graph of the AUT data comparing the material of Example 1 to a commercially available Huggies® Ultratrim® diaper.

One method of illustrating the absorption of the multifunctional material of this invention is to test it according to the AUT test and compare its absorbency to other known absorbents. FIG. 3 shows the results of AUT testing of the material of Example 1 below, and absorbent material taken from a Huggies® Ultratrim® diaper commercially available. The Ultratrim® diaper contained 32 percent Stockhausen FAVOR 880 superabsorbent and 68 percent southern softwood pulp and had a density of 0.183 g/cc and a basis weight of 814 gsm. FIG. 3 shows clearly that the Example 1 material did not absorb an insult as quickly as the Ultratrim® diaper, thereby allowing liquid to remain available and pass to a distribution component for eventual storage elsewhere.

The overall intake rate of the multifunctional material, and the ability to allow some liquid to pass immediately through to the distribution component is controlled by the multifunctional material permeability and capillary tension in relation to the materials in which the multifunctional material is in liquid contact. More particularly, the permeability of the multifunctional material should be greater than 100 Darcys or more preferably greater than 250 Darcys. The upper bound on the multifunctional material permeability is most likely about 10000 Darcys. The capillary tension of the multifunctional material must be greater than that of the surge and less than that of the distribution material in order to move liquid through the multifunctional material. Since surge materials generally have capillary tensions below 2 cm and distribution materials generally have capillary tensions above 15 cm, its preferred that the multifunctional material have a capillary tension which ranges from about 2 to about 15 centimeters, across the life of the system. In the initial dry state, the multifunctional material of Example 1, for example, has a 490 Darcy permeability and a 5.7 cm capillary tension. Note that capillary tension for materials containing superabsorbents is calculated by the method given in the test method section, not by equilibrium wicking.

In regard to permeability, its believed that as the slow superabsorbent swells, the multifunctional material caliper increases and the geometrical arrangement of superabsorbent particles and fibers opens the structure maintaining adequate permeability to provide the intake/pass through function on subsequent insults. Once the superabsorbent particles swell and the thickness of the material increases, by assuming that the added liquid resides within the swollen superabsorbent articles after an equilibration time of 30 minutes and measuring the thickness and wetted area, one can calculate the mass fractions of the components, the particle diameter and density, the web porosity, permeability, and capillary tension according to the test methods, for any web saturation level. In addition to maintaining adequate permeability for rapid uptake of liquid, the particle and fiber arrangement provides suitable void volume through multiple insults.

Capillary tension is important because the temporary holding function and the ability to desorb the surge material is believed to be controlled by the interstitial capillary matrix surrounding the superabsorbent. Liquid must be held in the capillaries created by the interstitial matrix at a capillary tension that is high enough so that liquid can be held and not released when the product suddenly undergoes positional changes. Further, the capillary tension level of the multifunctional material must remain above the capillary tension level of the surge material throughout the life of the system or product so that desorption of the surge material occurs and so that residual liquid is not available for rewetting of the surge material from the multifunctional material.

In addition to removeing liquid from the surge material, the multifunctional material must release liquid to the distribution material. The release of liquid from the multifunctional material to the distribution material for subsequent permanent storage elsewhere is effected by a competition between the superabsorbent liquid absorption rate and the capillary transfer or wicking rate to the underlying distribution material that are both pulling liquid out of the fibrous matrix surrounding the superabsorbent particles. If those rates are approximately matched, the amount of liquid that is released to the distribution layer is about the same as the amount which is stored in the multifunctional material. If the rates are not balanced, the liquid partitioning shifts. For example, if the superabsorbent absorbs faster than the distribution material wicks, more liquid will be permanently stored in the multifunctional material. These competing transfer rates make the capillary tension differential between the multifunctional material and the distribution material important to ensure the desired partitioning of liquid. Maintaining a sufficiently low capillary tension in the multifunctional material is, therefore, quite important. The nature of the superabsorbent as well as that of the fibrous matrix between them both affect the capillarity of the multifunctional material. It is important that the fibers of the matrix not collapse toward each other when the structure is wetted. Inclusion of fibers with high wet modulus and/or binder components aid in preventing such a collapse an so assist in maintaining acceptable capillarity. Capillarity is also related to the superabsorbent size and shape, because, in the case of particles, for example, large particles cause a more rapid drop in capillarity after an insult than do small particles as they swell. The functionality of the multifunctional material, therefore, is related to superabsorbent size and shape and speed of swelling. Rate of swelling is in turn influenced by superabsorbent composition and chemistry, the surface properties, e.g., the effect of any surface treatments, and the shape and size. Superabsorbents are available in a variety of shapes and forms such as beads, particles, foams, films and fibers. As a result, since a preferred range of superabsorbent content of the multifunctional material is given herein; it should be remembered that superabsorbent content above these ranges may also work if the capillarity and permeability requirements over its life are met.

Another factor the multifunctional material can greatly affect is the runoff rate for an insult. The runoff rate is quite important in personal care products such as diapers since liquids not absorbed by the product are free to escape from the product to soil the clothing or bedding of the wearer. The runoff rate from the multifunctional material is influenced by the multifunctional material capillarity among other factors, in that a low capillary tension causes liquid to enter the multifunctional material more slowly. Runoff rates for structures containign the multifunction material of this invention are below 25 ml for each 100 ml insult for three insults separated by 30 minutes using a sample size as given in the examples.

While it may appear obvious, it should be noted that in order to function effectively, the materials used in this invention must have sufficient contact to transfer liquid between them.

The multifunctional material must be mechanically stable in order to survive dry and wet use conditions. The integrity of the high superabsorbent containing composites may be provided by small amounts of thermally activated conjugate binder fiber, for example, or by any other suitable means such as with biconstituent fibers, liquid adhesives or heat activated film adhesives. Exemplary binder fibers include conjugate fibers of polyolefins and/or polyamides, and homopolymer microfibers like meltblown polypropylene fibers in a coform with the other ingredients to physically entangle and/or adhesively bond them.

As mentioned above, the basic structure of the multifunctional material of this invention is a unique blend of superabsorbent material, high bulk wet resilient pulp, and a structure stabilizing component such as a polyolefin binder fiber. The multifunctional material has a permeability of between about 100 and 10000 Darcys, a capillary tension between about 2 and 15 cm. Structurec conprising a surge and distribution material as well as the multifunctional material of this invention have a runoff rate of less than 25 ml per 100 ml insult, over its life. The "life" of the multifunctional material is considered to be three insults of 100 ml each separated by 30 minutes, for the purpose of this invention.

In order to achieve the required capillary tension and permeability, its preferred that the multifunctional material of this invention have between 30 and 75 weight percent of slow rate superabsorbent, between 25 and 70 weight percent of pulp and from a positive amount up to about 10 percent of a binder component. More particularly, the multifunctional material of this invention should have between 35 and 60 weight percent of slow rate superabsorbent, between 40 and 65 weight percent of pulp and between about 1 and 7 percent of a binder component. Still more particularly, the multifunctional material of this invention should have between 40 and 55 weight percent of slow rate superabsorbent, between 45 and 60 weight percent of pulp and between about 2 and 5 percent of a binder component. While not required, high wet modulus pulps are especially desirable. The material should have a density between about 0.05 and 0.5 g/cc. The basis weight of the material will vary depending on the product application but should generally be between about 200 and 700 gsm.

The multifunctional material may be made into a composite structure of the type used in personal care products by the addition of a surge material adjacent one side and a distribution material adjacent another side. It is important, of course, that any surge material used with the multifunctional material allows liquid to pass to the multifunctional material and/or readily releases liquid to the multifunctional material. The composite structure may also include a retention material adjacent the distribution material such that the distribution material moves liquid from the multifunctional material to the retention material.

In the examples that follow the component properties used in the calculations for permeability and capillary tension were as follows:

| Component | Shape | Diameter (mm) | Contact Angle | Density (g/cm$^3$) |
|---|---|---|---|---|
| CR 1654 pulp | Cylinder | 13.3 | 30 | 1.55 |
| CR 2054 pulp | Cylinder | 13.3 | 30 | 1.55 |
| HBAFF | Cylinder | 13.3 | 45 | 1.55 |
| Kymene treated CR1654 or 2054 | Cylinder | 13.3 | 60 | 1.55 |
| XL AFA-126-15* | Sphere | 1125 | 90 | 1.49 |
| Favor 880 | Sphere | 450 | 30 | 1.49 |
| 2 denier PE/PP Danaklon binder fiber | Cylinder | 17.5 | 90 | 0.925 |

Note that the shape and contact angles are approximated.
*XL AFA-126-15 polyacrylate bead is from The Dow Chemical Company of Midland, Michigan, 48674.

EXAMPLE 1

In this example, the multifunctional material consists of about 40 weight percent slow rate superabsorbent, about 57 weight percent Weyerhaeuser high bulk additive formaldehyde free pulp (HBAFF), and about 3 weight percent Danaklon short cut 2 denier polyethylene/polypropylene (PE/PP) sheath/core conjugate binder fiber.

The slow rate superabsorbent used was a 850 to 1400 micron suspension polymerized polyacrylate bead from The Dow Chemical Company of Midland, Mich. designated XL AFA-126-15. The slow rate was achieved by particle size, surface properties, and chemistry.

The high bulk additive pulp used was a crosslinked pulp fiber with enhanced wet modulus commercially available from the Weyerhaeuser Paper Company under the designation HBAFF. The pulp fibers are mechanically treated to impart a twisted and contorted nature to the fiber. A chemical treatment sets in this curl and twist, in addition to imparting added dry and wet stiffness and resilience to the fiber. The stiffened pulp fiber was combined with the binder fibers into a fiberizable pulp sheet. The binder fibers were from Danaklon a/s, located at Engdraget 22, KD-6800 Varde, Denmark, and were 2 denier conjugate PE/PP sheath/core fibers cut into 6 mm lengths.

The multifunctional material was airformed using a laboratory handsheet former to achieve an intermixed structure with a 620 gram/square meter (gsm) basis weight. The structure was stabilized in a constrained heated press operating at about 150° C. for 1 minute to activate the binder fiber and achieve a targeted density of about 0.1 g/cc. Any other satisfactory procedure known to those skilled in art may be used to produce the material.

In addition to the multifunctional material, two other materials were included in the functional testing to demonstrate the complete composite performance.

The first material was a surge layer of nonwoven fabric which was 90 weight percent 3 denier polyethylene/polyethylene terephthalate sheath/core conjugate staple fiber and 10 weight percent 1.5 denier rayon fiber. The surge layer fibers were carded and thermally bonded at about 270° F. (132° C.) to achieve a density of about 0.045 g/cc and about a 100 gsm basis weight. The surge material permeability was 1600 Darcys and it had a capillary tension of about 1.5 to 2 cm as measured by vertical wicking.

The surge structure was a 2 inch by 6 inch sample (5 cm×15 cm) which was layered to provide 100 ml of accessible void volume. Note that the test samples contained approximately 150 cc of total volume calculated by multiplying length times width times thickness. The test configuration, however, resulted in less than 10.2 cm of the total length accessible and usable to the insults resulting in approximately 100 cc of accessible void volume. It has been empirically found that samples in the MIST test cradle use about 2 inches of length on either side of the point of insult, or 4 inches (10.2 cm), not the entire sample length, which results in the calculated 100 cc of void volume.

The second material was a distribution layer which was a 200 gsm wetlaid pulp structure with about a 0.17 g/cc density. The distribution material permeability was about 50–100 Darcys and the capillary tension was greater than 15 cm as measured by vertical wicking.

Figure 4:
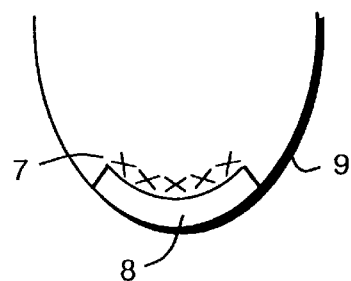
FIG. 4 is a side view of a diaper assembled in Example 1.

The three materials were layered together into a two inch (5 cm) width for functional testing simulating a narrow crotch design in the order of surge, multifunctional, and distribution materials. A side view is shown in FIG. 4 which shows the surge layer 7, multifunctional material 8 and distribution layer 9. The three components were placed in an acrylic cradle to simulate body curvature of a user such as an infant and tested according to the MIST evaluation test. The three components, with the surge on top, was insulted with 100 ml of 8.5 gram/liter saline solution at 20 cc/sec with a nozzle normal to the center of the surge material. The amount of runoff was recorded. The three components were immediately removed from the cradle and weighed individually to determine liquid partitioning between them. After weighing, they were reassembled and placed on a 40/60 fluff/superabsorbent pad in a horizontal position. Pressure was applied at 0.01 psig and the materials were removed from this configuration after 5 minutes, 15 minutes, and 30 minutes and separated to weigh each material individually to determine liquid partitioning across this time frame. The samples were reassembled in the same order after each weighing and were placed back into the cradle to again simulate body curvature. This test was repeated so that a total of three insults were introduced and liquid partitioning measured over 1.5 hours. The results are given in Table 1 where the data are given in grams of liquid in the material immediately after insult and at the 5, 15 and 30 minute marks for each layer for each of three insults. The runoff of the structure and of the multifunctional material, capillary tension and permeability after each insult is also given.

Note that the amounts shown in the tables may not add exactly to the expected or proper sum due to rounding.

TABLE 1

|  |  | g liquid in material | | | |
|---|---|---|---|---|---|
|  |  | Immediate | 5 min | 15 min | 30 min. |
| 1st Insult | Surge | 51.26 | 6.94 | 5.36 | 3.75 |
|  | Multifunctional | 27.76 | 9.72 | 11.43 | 12.88 |
|  | Distribution | 15.72 | 18.19 | 15.21 | 12.79 |
| 2nd Insult | Surge | 59.1 | 13. | 7.8 | 6.0 |
|  | Multifunctional | 40.0 | 32.5 | 26.8 | 28.4 |
|  | Distribution | 21.4 | 31. | 26.2 | 21.3 |
| 3rd Insult | Surge | 60.7 | 28.5 | 19.1 | 12.6 |
|  | Multifunctional | 53.5 | 37.4 | 38.2 | 39.2 |
|  | Distribution | 29.3 | 28.6 | 27.8 | 26.4 |

| Insult | 1st | 2nd | 3rd |
|---|---|---|---|
| Runoff | 4.1 | 6.8 | 9.3 |
| Capillary tension | 6.9 | 5.6 | 6.5 |
| Permeability | 490 | 1160 | 660 |
| Thickness (mm) | 6 | 10 | 12 |
| Wetted area (cm$^2$) | 0 | 56.4 | 56.4 |

Figure 5:
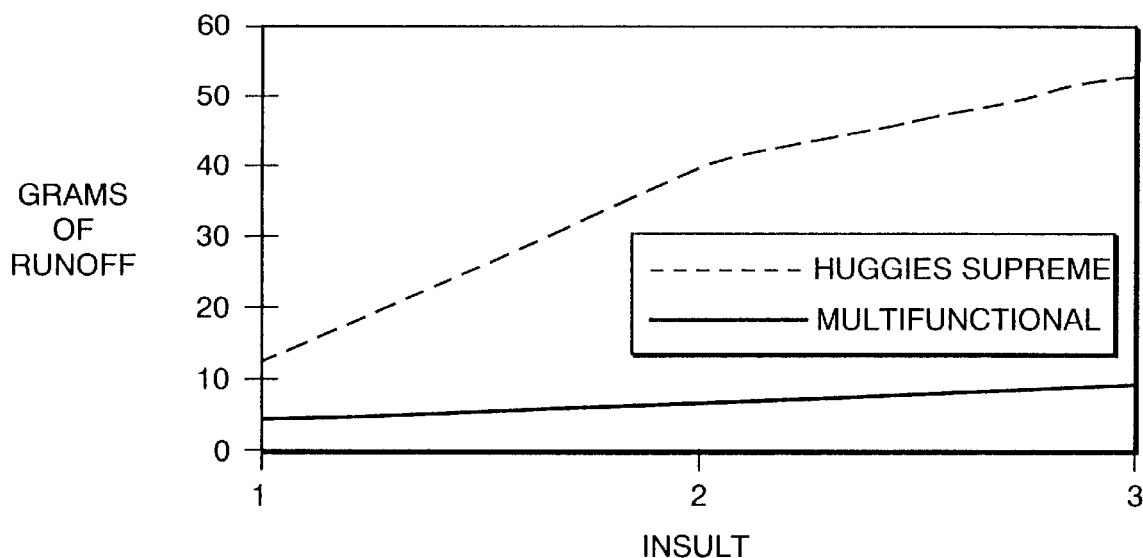
FIG. 5 is a graph of run-off results for Example 1 (solid line) and a Huggies® Supreme® diaper (dashed line).

FIG. 5 graphically illustrates run-off results from Table 1 as a solid line. This test data demonstrates low run-off values for the two inch wide material structure of this invention combined with the surge and distribution elements where the x axis is the number of the insult and the y axis is the runoff in grams. For comparison, FIG. 5 also shows run-off results for a four inch (10 cm) wide crotch, commercially available Huggies® Supreme® diaper from the Kimberly-Clark Corporation of Dallas, Tex. as a dashed line. These data demonstrate superior intake performance for the narrow crotch multifunctional composite across all three insult loadings.

Figure 6:
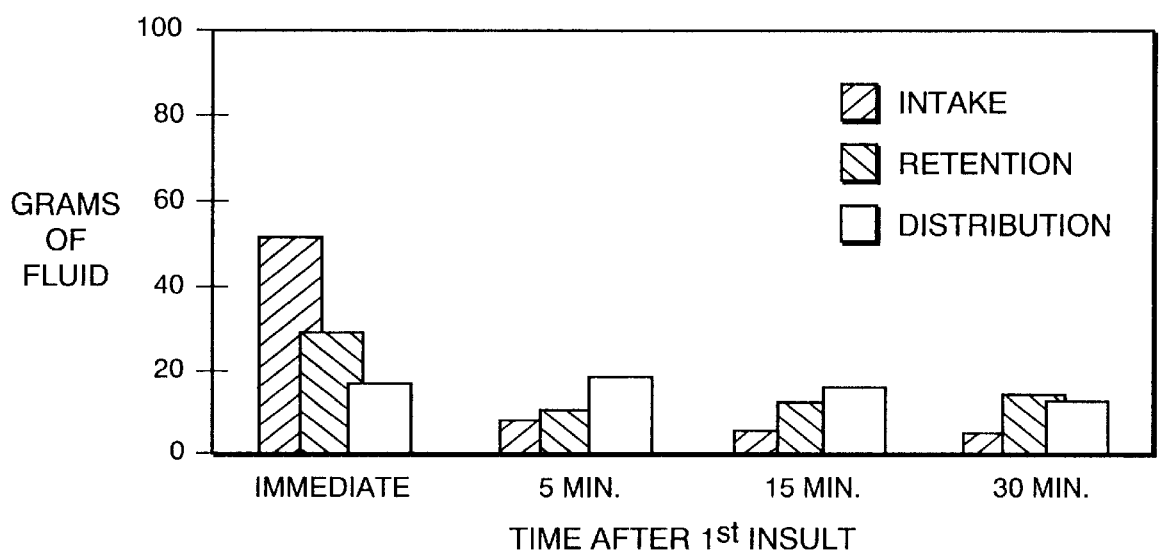
FIG. 6 is a graph illustrating the liquid partitioning in the structure of Example 1 after the first insult showing grams of liquid on the y-axis and time on the x-axis. The first bar in each set of three bars indicates liquid in the surge material. The second bar indicates the liquid in the multifunctional material. The third bar indicates the liquid in the distribution material.
Figure 7:
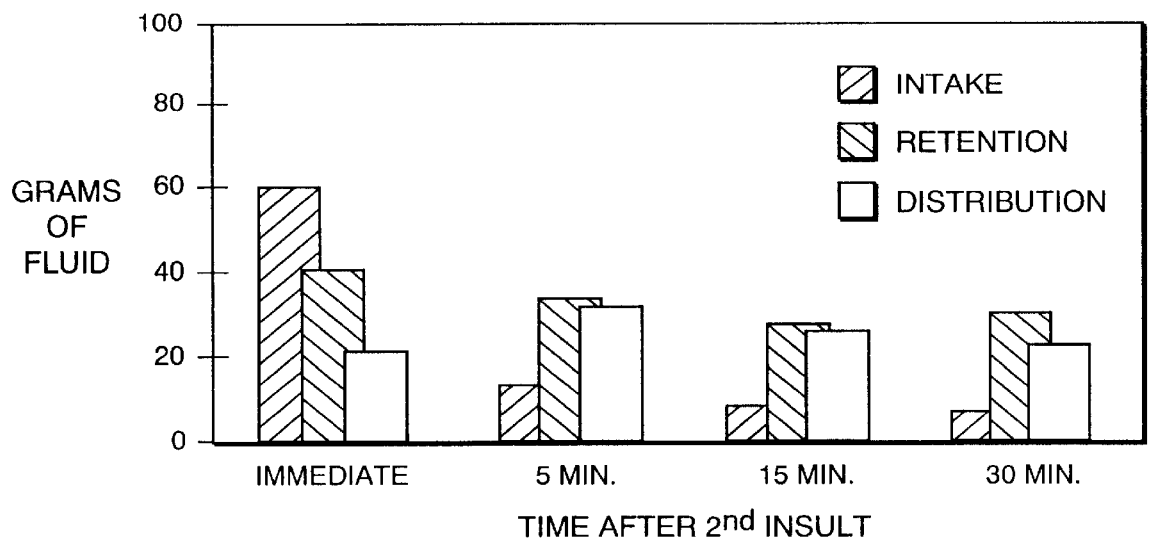
FIG. 7 is a graph illustrating the liquid partitioning in the structure of Example 1 after a second insult using the same designations as FIG. 6.
Figure 8:
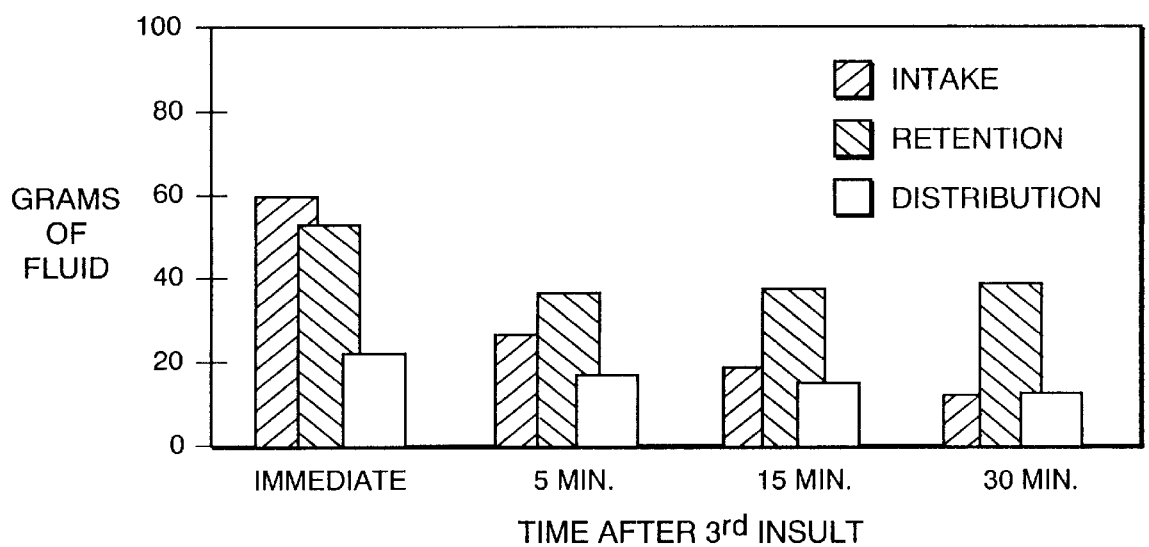
FIG. 8 is a graph illustrating the liquid partitioning in the structure of Example 1 after a third insult using the same designations as FIG. 6.

The graphs of FIGS. 6, 7 and 8 illustrate the unique liquid transfer characteristics of the multifunctional composite material including the immediate pass-through function, desorption of the surge material, and release of liquid from the multifunctional composite into the distribution material across time. FIGS. 6, 7 and 8 graphically show the data from Table 1 for the first, second and third insults, respectively, giving the immediate, 5, 15 and 30 minute liquid amounts in grams (y axis) in each layer. In FIGS. 6, 7 and 8 the intake or surge material is the first bar in each set, the multifunctional material is the second bar and the distribution material is the third bar.

The first set of columns in the FIG. 6 graph shows the liquid partitioning between the three components immediately after the first insult. These columns show that the surge material is holding about half or 50 ml of the 100 ml insult while the multifunctional material of this invention holds about 30 ml. About 15 ml is held within the distribution material below the multifunctional material. This illustrates that the multifunctional material has a sufficiently high starting permeability to allow some liquid to pass immediately through to the distribution material.

After a five minute desorption time, the second set of columns in the graph of FIG. 6 illustrates that the surge material has been desorbed to a level of about 5 ml. Because it is located above the multifunctional material throughout the entire testing procedure, the liquid is passing through the multifunctional material during this desorption phase.

The second set of columns in the graph of FIG. 6 show that the multifunctional material has released about 20 ml of liquid during the desorption phase. This supports the design criteria that a portion of the liquid is pulled out of the multifunctional material matrix while a portion is being transferred to the multifunctional material's slow superabsorbent for permanent storage.

The graph of FIG. 7 is an illustration of the liquid partitioning after the second 100 ml insult. The first set of bars shows the surge material again picking up about 50 ml. Note that the first bar indicates about 55 ml total but also that the surge material was holding 5 ml after the first insult making the total pick-up of 50 ml consistent with first insult performance. The second bar within the first set of bars illustrates the multifunctional material picking up about 30 mls similar to its first insult performance. Note that while this bar shows 40 ml, the multifunctional material was holding 10 mls at the end of the first desorption cycle so that only 30 ml was picked up during second insult.

The distribution material shows similar saturation levels throughout all desorption testing. During the desorption testing, the distribution material is in contact with a desorption retention pad used in this testing configuration. Once the distribution material is saturated in the first insult, its saturation level remains approximately consistent because it is being fed by liquid being released from the multifunctional composite, and it is releasing liquid to the retention material at a similar rate.

The graph of FIG. 8 illustrates the desorption phase liquid partitioning after the third insult and reconfirms the data conclusions discussed in regard to FIGS. 6 and 7.

EXAMPLE 2

In this example, the multifunctional material consisted of about 40 weight percent of the same slow rate superabsorbent as in Example 1 and about 60 weight percent of Kimberly-Clark's CR2054 southern softwood fluff which had been treated with 0.2 weight percent of a liquid binder. The particular liquid binder used was Kymene® 557LX binder available from Hercules Inc. of Wilmington, Del. The liquid binder was activated by the addition of 20 weight percent water and heating to about 105° C. for about 10 minutes.

The multifunctional material was airformed using a laboratory handsheet former to achieve an intermixed structure with a 440 gsm basis weight. The structure had a targeted density of about 0.22 g/cc.

This multifunctional material was tested with the same surge and distribution material layers as in Example 1 in the same manner given therein and the results are given in Table 2.

TABLE 2

|  |  | g liquid in material | | | |
|---|---|---|---|---|---|
|  |  | Immediate | 5 min | 15 min | 30 min. |
| 1st Insult | Surge | 44.4 | 4.7 | 3.5 | 3.1 |
|  | Multifunctional | 19.8 | 19.7 | 22.0 | 24.3 |
|  | Distribution | 14.4 | 21.6 | 17.7 | 10.6 |
| 2nd Insult | Surge | 51.4 | 5.5 | 3.9 | 3.4 |
|  | Multifunctional | 45.4 | 40.5 | 41. | 41.9 |

TABLE 2-continued

|  |  |  |  |  |  |
|---|---|---|---|---|---|
|  | Distribution | 23.0 | 26.8 | 24.0 | 20.2 |
| 3rd Insult | Surge | 54.6 | 6.7 | 4.6 | 4.1 |
|  | Multifunctional | 58.8 | 55.4 | 53.8 | 53.1 |
|  | Distribution | 27.2 | 29.8 | 27.4 | 23.2 |

| Insult | 1st | 2nd | 3rd |
|---|---|---|---|
| Runoff | 19 | 20 | 23 |
| Cap. tension | 16.3 | 6.1 | 6.9 |
| Permeability | 140 | 840 | 660 |
| Thickness (mm) | 2 | 7 | 8.4 |
| Wetted area (cm$^2$) | 0 | 118 | 118 |

EXAMPLE 3

In this example, the multifunctional material consisted of about 60 weight percent of the same slow rate superabsorbent as in Example 1, about 37 weight percent of Kimberly-Clark's CR1654 fluff and about 3 percent Danaklon conjugate binder fiber.

The multifunctional material was airformed using a laboratory handsheet former to achieve an intermixed structure with a 660 gsm basis weight. The structure had a targeted density of about 0.12 g/cc.

This multifunctional material was tested with the same surge and distribution material layers as in Example 1 in the same manner given therein and the results are given in Table 3. Note that although the capillary tension and permeability after each insult were not calculated, it is anticipated that they would be similar to the values in Example 1 due to the similarity in composition of the materials.

TABLE 3

|  |  | g liquid in material |  |  |  |
|---|---|---|---|---|---|
|  |  | Immediate | 5 min | 15 min | 30 min |
| 1st Insult | Surge | 51.9 | 4.9 | 2.7 | 2.0 |
|  | Multifunctional | 20.3 | 12.8 | 16.7 | 18.38 |
|  | Distribution | 14.6 | 18.3 | 13.5 | 10. |
| 2nd Insult | Surge | 58. | 8.4 | 5.2 | 3.8 |
|  | Multifunctional | 39.7 | 32.2 | 35.6 | 37.9 |
|  | Distribution | 19.6 | 20.7 | 15.8 | 11.9 |
| 3rd Insult | Surge | 64.2 | 22.9 | 11.9 | 6.4 |
|  | Multifunctional | 58.6 | 50.8 | 53.9 | 56.9 |
|  | Distribution | 20. | 21.1 | 20.3 | 18.1 |

| Insult | 1st | 2nd | 3rd |
|---|---|---|---|
| Runoff | 10.5 | 9.8 | 7.4 |
| Cap. tension | 5.4 | NA* | NA |
| Permeability | 800 | NA | NA |
| Thickness (mm) | 0.5 | NA | NA |
| Wetted area (cm$^2$) | 0 | NA | NA |

*Note NA means not available.

EXAMPLE 4

In this example, the multifunctional material consisted of about 60 weight percent of slow rate superabsorbent about 37 weight percent of the same pulp as in Example 1 and about 3 percent Danaklon conjugate binder fiber.

The slow rate superabsorbent used was the same as used in Example 1.

The multifunctional material was airformed using a laboratory handsheet former to achieve an intermixed structure with a 440 gsm basis weight. The structure had a targeted density of about 0.09 g/cc.

This multifunctional material was tested with the same surge and distribution material layers as in Example 1 in the same manner given therein and the results are given in Table 4.

TABLE 4

|  |  | g liquid in material |  |  |  |
|---|---|---|---|---|---|
|  |  | Immediate | 5 min | 15 min | 30 min. |
| 1st Insult | Surge | 53.4 | 4.3 | 3.4 | 2.7 |
|  | Multifunctional | 21.9 | 13.3 | 14.4 | 15.1 |
|  | Distribution | 15.2 | 12.5 | 10.1 | 8.5 |
| 2nd Insult | Surge | 58.2 | 7.4 | 4.8 | 4. |
|  | Multifunctional | 38.0 | 31.4 | 32.7 | 33.7 |
|  | Distribution | 17.9 | 27.8 | 19.3 | 15.3 |
| 3rd Insult | Surge | 65.4 | 11.0 | 6.7 | 5.1 |
|  | Multifunctional | 53. | 44.2 | 45.9 | 47.0 |
|  | Distribution | 24.2 | 25.3 | 22.8 | 21.9 |

| Insult | 1st | 2nd | 3rd |
|---|---|---|---|
| Runoff | 7.6 | 6.9 | 5.5 |
| Cap. tension | 3.8 | 2.0 | 2.3 |
| Permeability | 1370 | 9150 | 5980 |
| Thickness (mm) | 5 | 12.5 | 14 |
| Wetted area (cm$^2$) | 0 | 84 | 84 |

EXAMPLE 5

In this example, the multifunctional material consisted of about 70 weight percent of the same slow rate superabsorbent as in Example 4, about 27 weight percent of the same pulp as in Example 1 and about 3 percent Danakion conjugate binder fiber.

The multifunctional material was airformed using a laboratory handsheet former to achieve an intermixed structure with a 500 gsm basis weight. The structure had a targeted density of about 0.12 g/cc.

This multifunctional material was tested with the same surge and distribution material layers as in Example 1 in the same manner given therein and the results are given in Table 5. Note that the low capillary tension of the multifunctional material impeded the desorption of liquid from the surge layer. This low capillary tension is believed to be caused by the large and hydrophobic nature of the superabsorbent particle used in this Example 5 to achieve the desired slow rate. If the multifunctional material's slow rate were achieved by a method other than particle size and hydrophobicity, a multifunctional material having 70 weight percent superabsorbent should function acceptably well within the metes and bounds of the invention. In fact, using the second and third insult information from Example 5 which is needed to predict permeability and capillarity, and assuming a multifunctional material having 70 weight percent superabsorbent with a size of 450 microns and a contact angle of 30 degrees, capillary tension and permeability conforming with the invention were calculated and are shown below (note that since an actual material was not made, runoff data is absent):

| Insult | 1st | 2$^{nd}$ | 3$^{rd}$ |
|---|---|---|---|
| Cap. Tension | 4.1 | 3.1 | 2.9 |
| Permeability | 1325 | 3590 | 3880 |

TABLE 5

|  |  | g liquid in material | | | |
|---|---|---|---|---|---|
|  |  | Immediate | 5 min | 15 min | 30 min. |
| 1st Insult | Surge | 56 | 38.1 | 34. | 31.1 |
|  | Multifunctional | 13.9 | 9.9 | 13.7 | 16.5 |
|  | Distribution | 13.3 | 13. | 9.7 | 8.3 |
| 2nd Insult | Surge | 60.4 | 55. | 50.6 | 46.7 |
|  | Multifunctional | 31.1 | 25.2 | 28.5 | 30.9 |
|  | Distribution | 18. | 14.4 | 12.4 | 10.9 |
| 3rd Insult | Surge | 65.8 | 56.2 | 52.6 | 49.7 |
|  | Multifunctional | 48.5 | 38.6 | 40.5 | 41.6 |
|  | Distribution | 20.5 | 13.5 | 11.9 | 10.0 |

| Insult | 1st | 2nd | 3rd |
|---|---|---|---|
| Runoff | 16.5 | 43.3 | 43.4 |
| Cap. Tension | 3.9 | 2.4 | 2.1 |
| Permeability | 1490 | 5670 | 7060 |
| Thickness (mm) | 4 | 10 | 14 |
| Wetted area (cm$^2$) | 0 | 71.6 | 71.6 |

Figure 9:
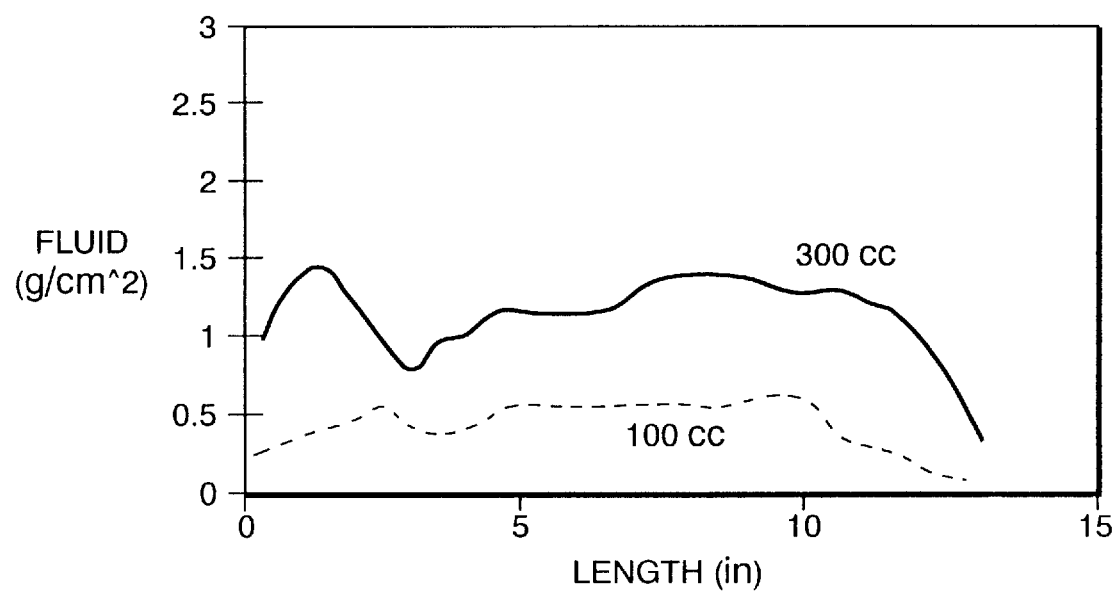
FIG. 9 compares in graphical form the liquid profile of a system using the material of this invention with a 100 ml insult (dashed line) and after three 100 ml insults (solid line). The distance from the insult site is indicated on the x-axis.

Finally, the graph of FIG. 9 shows liquid distribution data from an entire absorbent system with the surge, multifunctional and distribution materials of Example 1 placed into a diaper chassis and tested on babies. This absorbent system is as shown in FIG. 1 and has the permanent storage retention composites in place. The permanent storage retention composites were made from 60 weight percent Stockhausen Company's FAVOR 870 highly crosslinked surface superabsorbent, 38 weight percent Kimberly-Clark Corporation's CR2054 pulp and about 2 weight percent Kymene® liquid binder. The diapers were placed on 20 babies and insulted with three 100 ml insults of 8.5 g/l saline solution 30 minutes apart. The diapers were removed from the babies at the end of 30 minutes and 90 minutes and x-rayed to determine liquid distribution. The graph of FIG. 9 shows liquid has moved to the ends of the product for both 100 ml and 300 ml insults. This illustrates that the multifunctional material liquid partitioning characteristics function in full absorbent systems and allow liquid distribution to occur under simulated real use conditions.

In summary, the example multifunctional material data illustrate the unique forced flow liquid handling and capillary flow liquid partitioning characteristics of the material and structure of this invention. The data illustrate low run-off values for a narrow crotch multifunctional composite structure. In addition, the example bench data shows that the composite structure has a liquid pass through function, desorbs the surge material across time frames consistent with user conditions (e.g. about 90 minutes), and releases liquid from its interstitial matrix for distribution to remote storage locations instead of holding the majority of an insult in the intake area. The distribution benefit of this multifunctional material is demonstrated in full absorbent system testing within a diaper chassis construction on real infants.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A multifunctional material comprising superabsorbent, pulp and a binder component wherein said multifunctional material has a permeability between 100 and 10000 Darcys, a capillary tension between about 2 and 15 cm over its life.

2. The material of claim 1 having between 30 and 75 weight percent of a superabsorbent, between 25 and 70 weight percent of pulp and from a positive amount up to about 10 percent of a binder component.

3. The material of claim 1 having a density between about 0.05 and 0.5 g/cc.

4. The material of claim 1 having a basis weight between about 200 and 700 gsm.

5. The material of claim 1 wherein said superabsorbent has an absorption time index of greater than 5 minutes.

6. The material of claim 1 wherein said superabsorbent has an absorption time index of greater than 10 minutes.

7. The material of claim 1 wherein said superabsorbent is selected from the group consisting of particles, beads and fibers.

8. The material of claim 1 wherein said binder component is selected from the group consisting of liquid and fiber adhesives.

9. The material of claim 8 wherein said binder is a heat activated adhesive fiber.

10. The material of claim 9 wherein said fiber is selected from the group consisting of polyethylenelpolyethylene terephthalate, polyester/polyethylene terephthalate, and polyethylene/polypropylene.

11. A composite structure for personal care products comprising a surge material adjacent to the multifunctional material of claim 1 which is adjacent to a distribution material.

12. The composite structure of claim 11 wherein said multifunctional material has a capillary tension greater than said surge material and less than said distribution material.

13. The composite structure of claim 11 further comprising a retention material adjacent to said distribution material such that said distribution material distributes liquid from said multifunctional material to said retention material.

14. A personal care product selected from the group consisting of diapers, training pants, absorbent underpants, adult incontinence products and feminine hygiene products comprising the material of claim 1.

15. The product of claim 14 wherein said personal care product is a feminine hygiene product.

16. The product of claim 14 wherein said personal care product is an adult incontinence product.

17. The product of claim 14 wherein said personal care product is a diaper.

18. The diaper of claim 17 having a crotch width of at most 7.6 cm.

19. A narrow crotch diaper comprising;
a surge material,
a multifunctional material layer in liquid communication with said surge material and comprising between 35 and 60 weight percent of a slow rate superabsorbent, between 40 and 65 weight percent of pulp and between about 1 and 7 percent of a binder component, wherein said multifunctional materials has a permeability between 250 and 10000 Darcys, and a capillary tension between about 2 and 15 cm, over its life,
a distribution layer, retention material in liquid communication with said distribution layer and which stores liquid, and;

wherein said diaper has a crotch having a width of at most 5 cm and a runoff rate of less than 25 ml per a 100 ml insult.

20. A narrow crotch diaper comprising;

a surge material capable of handling an incoming insult of between about 60 and 100 cc at a volumetric flow rate of from about 5 to 20 cc/sec, a multifunctional material layer in liquid communication with said surge material and having a liquid pass through function which also desorbs the surge material across time frames consistent with user conditions and releases liquid for distribution to remote storage locations, a distribution layer in liquid communication with said multifunctional material having a capillary tension greater than 15 cm which moves liquid from said multifunctional material to remote storage locations, retention material in liquid communication with said distribution layer which stores liquid, wherein said diaper has a crotch having a width of at most 5 cm.

* * * * *

UNITED STATES PATENT AND TRADEMARK OFFICE
CERTIFICATE OF CORRECTION

PATENT NO. : 5,843,063
DATED : December 1, 1998
INVENTOR(S) : Richard A. Anderson et al.

It is certified that error appears in the above-identified patent and that said Letters Patent is hereby corrected as shown below:

Column 17, Line 46, "rewefting" should read -- rewetting --

Signed and Sealed this

Thirtieth Day of March, 1999

Attest:

Q. TODD DICKINSON

*Attesting Officer*        *Acting Commissioner of Patents and Trademarks*